US011390857B2

(12) United States Patent
Larsen et al.

(10) Patent No.: US 11,390,857 B2
(45) Date of Patent: Jul. 19, 2022

(54) DNA POLYMERASES

(71) Applicant: UNIVERSITETET I TROMSØ—NORGES ARTISKE UNIVERSITET, Tromsø (NO)

(72) Inventors: Atle Noralf Larsen, Tromsø (NO); Yvonne Piotrowski, Tromsø (NO)

(73) Assignee: UNIVERSITETET I TROMSØ—NORGES ARTISKE UNIVERSITET, Tromsø (NO)

( * ) Notice: Subject to any disclaimer, the term of this patent is extended or adjusted under 35 U.S.C. 154(b) by 0 days.

(21) Appl. No.: 16/772,690

(22) PCT Filed: Dec. 17, 2018

(86) PCT No.: PCT/EP2018/085342
§ 371 (c)(1),
(2) Date: Jun. 12, 2020

(87) PCT Pub. No.: WO2019/115834
PCT Pub. Date: Jun. 20, 2019

(65) Prior Publication Data
US 2020/0325459 A1  Oct. 15, 2020

(30) Foreign Application Priority Data
Dec. 15, 2017 (GB) ..................... 1721053

(51) Int. Cl.
| C12N 9/12 | (2006.01) |
| C12Q 1/6844 | (2018.01) |
| C12N 1/21 | (2006.01) |
| C12N 15/54 | (2006.01) |

(52) U.S. Cl.
CPC ......... *C12N 9/1252* (2013.01); *C12Q 1/6844* (2013.01); *C12Q 2521/101* (2013.01); *C12Y 207/07007* (2013.01)

(58) Field of Classification Search
None
See application file for complete search history.

(56) References Cited

U.S. PATENT DOCUMENTS

| 6,485,909 B1 | 11/2002 | Hong et al. |
| 6,818,431 B1 | 11/2004 | Hong et al. |
| 8,993,298 B1 | 3/2015 | Ong et al. |
| 9,127,258 B2 | 9/2015 | Ong et al. |
| 9,157,073 B1 | 10/2015 | Ong et al. |
| 2008/0311626 A1 | 12/2008 | Hjorleifsdottir et al. |
| 2010/0047862 A1* | 2/2010 | Hayashizaki ........ C12N 9/1276 435/69.1 |
| 2013/0040365 A1* | 2/2013 | Vander Horn ......... C12Q 1/686 435/194 |
| 2015/0094211 A1* | 4/2015 | Vander Horn ....... C12Q 1/6869 506/2 |

FOREIGN PATENT DOCUMENTS

| WO | 2006030455 A1 | 3/2006 | |
| WO | 2015/048763 A1 | 4/2015 | |
| WO | 2016/077324 A1 | 5/2016 | |
| WO | 2016183294 A1 | 11/2016 | |
| WO | 2017/058810 A2 | 4/2017 | |
| WO | 2017148861 A1 | 9/2017 | |
| WO | 2017162765 A1 | 9/2017 | |
| WO | WO-2017162765 A1 * | 9/2017 | ........... C12N 9/1252 |

OTHER PUBLICATIONS

Burgess et al., Insights into the *Geobacillus stearothermophilus* species based on phylogenomic principles, BMC Microbiol. 17, 2017, 140. (Year: 2017).*
Puigbo et al., Optimizer: a web server for optimizing the codon usage of DNA sequences, Nucleic Acids Res. 35, 2007, W126-W131. (Year: 2007).*
Uniprot, Accession No. A0A1I5YQ56, 2017, www.uniprot.org. (Year: 2017).*
International Search Report and Written Opinion dated Feb. 19, 2019, International Application No. PCT/EP2018/085342, pp. 1-12.
UKIPO Combined Search & Examination Report dated Nov. 7, 2018, United Kingdom Application No. GB1721053.5, pp. 1-17.
Monica Amblar et al., "Purification and properties of the 5'-3' exonuclease D190—A mutant of DNA polmerase I from *Streptococcus pneumoniae*", Eur. J. Biochem., 252, 1998, pp. 124-132.
UniProtKB—Q45458 (Q45458_GEOSE), pp. 1-9, 2020.
Kamalendra Singh et al., "Participation of the Fingers Subdomain of *Escherichia coli* DNA Polymerase I in the Strand Displacement Synthesis of DNA" The Journal of Biological Chemistry, vol. 282, No. 14, Apr. 2007, pp. 10594-10604.
DNA polymerase I [Ureibacillus thermosphaericus], NCBI Reference Sequence: WP_016837139.1, pp. 1-3.
James R. Kiefer et al., "Crystal Structure of a thermostable Bacillus DNA polymerase I large fragment at 2.1 A resolution", Structure, vol. 5, No. 1, 1997, pp. 95-108.
Han Bei et al., "Preliminary characterization of a thermostable DNA polymerase I from a mesophilic Bacillus sphaericus strain C3-41", Archives of Microbiology, 186, Oct. 2006, pp. 203-209.

(Continued)

*Primary Examiner* — Todd M Epstein
(74) *Attorney, Agent, or Firm* — Siepmann Ip, PLLC; Thomas J. Siepmann

(57) ABSTRACT

The present invention provides a DNA polymerase including the sequence of SEQ ID NO. 1 or a sequence which is at least 70% identical thereto, but wherein the aspartic acid residue at position 18 of SEQ ID NO. 1, or the equivalent aspartic acid residue in other sequences, has been replaced by a non-negatively charged amino acid residue. It further provides DNA polymerases comprising the amino acid sequences of SEQ ID NO. 2, 11 and 12 and variants thereof. The present invention also provides nucleic acids encoding the DNA polymerases, a method of producing said DNA polymerases, and compositions, expression vectors and host cells or viruses comprising said DNA polymerases. The present invention also provides uses of said DNA polymerases in nucleotide polymerisation, amplification and sequencing reactions.

17 Claims, 9 Drawing Sheets

Specification includes a Sequence Listing.

(56) References Cited

OTHER PUBLICATIONS

Bacillus sphaericus strain C3-41 DNA polymerase I (poIA) gene, complete cds, GenBank DQ309765.1, pp. 1-2, 2019.
Pooria Gill et al., "Nucleic Acid Isothermal Amplification Technologies—A Review", Nucleosides, Nucleotides, and Nucleic Acids, 27, 2008, pp. 224-243.
Pascal Craw et al., "Isothermal nucleic acid amplification technologies for point-of-care diagnostics: a critical review", Lab on a Chip, 12, 2012, pp. 2469-2486.
Hector Daved De Paz et al., "Molecular isothermal techniques for combating infectious diseases: towards low-cost point-of-care diagnostics", Expert Rev. Mol. Diagn., 14(7), 2014, pp. 827-843.
Lei Yan et al., "Isothermal amplified detection of DNA and RNA", Molecular BioSystems, 10, Feb. 2014, pp. 970-1003.
Wei Liu et al., "Polymerase Spiral Reaction (PSR): A novel isothermal nucleic acid amplification method", Scientific Reports, 5:12723, Jul. 2015, pp. 1-8.
Zhaochun Ma et al., "Isothermal amplification method for next-generation sequencing", PNAS, vol. 110, No. 35, Aug. 2013, pp. 14320-14323.

\* cited by examiner

| | | | |
|---|---|---|---|
| PB | : MRRAAKAVNFGIVYGISDDYGLSQNLDITRKEA | 32 | SEQ ID NO:1 |
| Bacillus_sp_C3_41 | : MRRAAKAVNFGIVYGISDDYGLSQNLDITRKEA | 32 | SEQ ID NO:6 |
| Ubts | : MRRAAKAVNFGIIYGISDDYGLSQNLDISRKEA | 32 | SEQ ID NO:7 |
| BSU | : MRRQAKAVNFGIVYGISDDYGLSQNLGITRKEA | 32 | SEQ ID NO:8 |
| Bsm | : MRRQAKAVNFGIVYGISDDYGLSQNLGITRKEA | 32 | SEQ ID NO:9 |
| Bst | : MRRQAKAVNFGIVYGISDDYGLAQNLNISRKEA | 32 | SEQ ID NO:10 |

SEQUENCE LISTING

<160> NUMBER OF SEQ ID NOS: 20

<210> SEQ ID NO 1
<211> LENGTH: 32
<212> TYPE: PRT
<213> ORGANISM: Psychrobacillus sp.

<400> SEQUENCE: 1

Met Arg Arg Ala Ala Lys Ala Val Asn Phe Gly Ile Val Tyr Gly Ile
1               5                   10                  15

Ser Asp Tyr Gly Leu Ser Gln Asn Leu Asp Ile Thr Arg Lys Glu Ala
                20                  25                  30

<210> SEQ ID NO 2
<211> LENGTH: 580
<212> TYPE: PRT
<213> ORGANISM: Psychrobacillus sp.

<400> SEQUENCE: 2

Thr Glu Val Ala Phe Glu Ile Val Glu Ile Asp Ser Thr Ile Leu
1               5                   10                  15

Asp Lys Val Met Ser Val His Leu Glu Met Tyr Asp Gly Gln Tyr His
                20                  25                  30

Thr Ser Glu Leu Leu Gly Ile Ala Leu Ser Asp Gly Glu Lys Gly Tyr

```
            35                  40                  45
Phe Ala Pro Ala Asp Ile Ala Phe Gln Ser Lys Asp Phe Cys Ser Trp
 50                  55                  60

Leu Glu Asn Ala Thr Asn Lys Lys Tyr Leu Ala Asp Ser Lys Ala Thr
 65                  70                  75                  80

Gln Ala Val Ser Arg Lys His Asn Val Asn Val His Gly Val Glu Phe
                 85                  90                  95

Asp Leu Leu Leu Ala Ala Tyr Ile Val Asn Pro Ala Ile Ser Ser Glu
                100                 105                 110

Asp Val Ala Ala Ile Ala Lys Glu Phe Gly Tyr Phe Asn Leu Leu Thr
                115                 120                 125

Asn Asp Ser Val Tyr Gly Lys Gly Ala Lys Lys Thr Ala Pro Glu Ile
            130                 135                 140

Glu Lys Ile Ala Glu His Ala Val Arg Lys Ala Arg Ala Ile Trp Asp
145                 150                 155                 160

Leu Lys Glu Lys Leu Glu Val Lys Leu Glu Glu Asn Glu Gln Tyr Ala
                165                 170                 175

Leu Tyr Lys Glu Ile Glu Leu Pro Leu Ala Ser Ile Leu Gly Thr Met
                180                 185                 190

Glu Ser Asp Gly Val Leu Val Asp Lys Gln Ile Leu Val Glu Met Gly
            195                 200                 205

His Glu Leu Asn Ile Lys Leu Arg Ala Ile Glu Gln Asp Ile Tyr Ala
210                 215                 220

Leu Ala Gly Glu Thr Phe Asn Ile Asn Ser Pro Lys Gln Leu Gly Val
225                 230                 235                 240

Ile Leu Phe Glu Lys Ile Gly Leu Thr Pro Ile Lys Lys Thr Lys Thr
                245                 250                 255

Gly Tyr Ser Thr Ala Ala Asp Val Leu Glu Lys Leu Ala Ser Glu His
            260                 265                 270

Glu Ile Ile Glu Gln Ile Leu Leu Tyr Arg Gln Leu Gly Lys Leu Asn
            275                 280                 285

Ser Thr Tyr Ile Glu Gly Leu Leu Lys Glu Ile His Glu Asp Asp Gly
    290                 295                 300

Lys Ile His Thr Arg Tyr Gln Gln Ala Leu Thr Ser Thr Gly Arg Leu
305                 310                 315                 320

Ser Ser Ile Asn Pro Asn Leu Gln Asn Ile Pro Val Arg Leu Glu Glu
                325                 330                 335

Gly Arg Lys Ile Arg Lys Ala Phe Val Pro Ser Gln Pro Gly Trp Val
            340                 345                 350

Met Phe Ala Ala Asp Tyr Ser Gln Ile Glu Leu Arg Val Leu Ala His
            355                 360                 365

Met Ser Glu Asp Glu Asn Leu Val Glu Ala Phe Asn Asn Asp Leu Asp
    370                 375                 380

Ile His Thr Lys Thr Ala Met Asp Val Phe His Val Glu Gln Glu Ala
385                 390                 395                 400

Val Thr Ser Asp Met Arg Arg Ala Ala Lys Ala Val Asn Phe Gly Ile
                405                 410                 415

Val Tyr Gly Ile Ser Asp Tyr Gly Leu Ser Gln Asn Leu Asp Ile Thr
            420                 425                 430

Arg Lys Glu Ala Ala Thr Phe Ile Glu Asn Tyr Leu Asn Ser Phe Pro
            435                 440                 445

Gly Val Lys Gly Tyr Met Asp Asp Ile Val Gln Asp Ala Lys Gln Thr
            450                 455                 460
```

```
Gly Tyr Val Thr Thr Ile Leu Asn Arg Arg Tyr Leu Pro Glu Ile
465                 470                 475                 480

Thr Ser Ser Asn Phe Asn Leu Arg Ser Phe Ala Glu Arg Thr Ala Met
            485                 490                 495

Asn Thr Pro Ile Gln Gly Ser Ala Ala Asp Ile Ile Lys Lys Ala Met
        500                 505                 510

Ile Asp Met Ala Glu Arg Leu Ile Ser Glu Asn Met Gln Thr Lys Met
    515                 520                 525

Leu Leu Gln Val His Asp Glu Leu Ile Phe Glu Ala Pro Pro Glu Glu
530                 535                 540

Ile Ala Met Leu Glu Lys Ile Val Pro Glu Val Met Glu Asn Ala Ile
545                 550                 555                 560

Lys Leu Ile Val Pro Leu Lys Val Asp Tyr Ala Phe Gly Ser Ser Trp
                565                 570                 575

Tyr Asp Thr Lys
            580
```

<210> SEQ ID NO 3
<211> LENGTH: 1743
<212> TYPE: DNA
<213> ORGANISM: Psychrobacillus sp.

<400> SEQUENCE: 3

```
acagaagtag cattcgagat tgttgaagaa attgactcta caatattaga taaagtaatg      60
tcagtccatt tagaaatgta tgatgggcaa tatcatacaa gcgaattatt aggtattgct     120
ttatcagatg gagaaaaggg ttattttgct cctgctgata tagcttttca atcgaaggat     180
ttttgttctt ggttagaaaa tgctacgaat aaaaagtatt tagcagactc caaagcaaca     240
caagcagtga gtagaaaaca taatgtgaat gtacatggag tggaattcga ccttctttta     300
gcagcgtata tagtaaatcc tgctatctct tcagaggatg ttgctgctat tgctaaagaa     360
tttggatatt ttaacttgct gacaaacgat agtgtttatg ggaaaggtgc aaaaaaaacc     420
gcacctgaaa tcgagaaaat tgcagaacat gccgtaagaa aagcaagggc tatttgggac     480
ttgaagaaaa gttagaagt aaaactggaa gaaaatgaac aatatgcgtt gtataaagaa     540
atagagctac cgcttgcatc tatccttggt acgatggaat cagatggggt gctggtggat     600
aaacaaattc ttgtagaaat gggtcatgag cttaatatta agttacgagc gattgaacaa     660
gacatttatg cgttagctgg tgaaacgttt aatattaatt cacctaaaca attaggtgta     720
atactatttg aaaaaattgg tcttacccct attaaaaaga caaaaacggg ctattcaact     780
gcagcagatg ttttggaaaa actagcaagt gaacatgaaa taatagagca attttacta     840 tatcgtcaat taggtaaact caattccaca tatatcgaag gattattaaa agagattcat     900
gaagatgatg ggaagatcca tacccgatat caacaagccc taacttcaac tgggcgtttg     960
agttcgatca atccaaacct tcaaaatata ccagttcgtt tagaagaagg tagaaaaata    1020
cgtaaagcct tgttccttc acaaccggga tgggtaatgt ttgcggcgga ttactctcaa    1080
attgaattgc gtgttcttgc ccatatgtct gaggatgaaa acctggtaga agcttttaat    1140
aatgatctgg atattcatac taaaacggct atggatgtat ccatgtgga gcaggaagca    1200 gtaacgtccg atatgcgccg tgctgctaag gcagttaact tgggattgt gtatggtatt    1260 agtgattatg gttatcaca aaacctagat attactagaa agaagcggc gacatttatc    1320 gagaattatt taaatagctt cccaggtgta aaaggatata tggatgatat cgttcaagat    1380
```

-continued

| | | |
|---|---|---|
| gcgaaacaaa caggctacgt tacaacaatt ttgaatagac gaagatattt gcctgaaata | 1440 |
| acaagttcta actttaatct ccgcagtttt gcagaacgta ctgctatgaa tacaccaatt | 1500 |
| caagggagtg cagccgatat tattaaaaaa gcaatgatcg atatggcgga agattaata | 1560 |
| tcagaaaata tgcagaccaa aatgctacta caagtacatg atgaattaat ttttgaggct | 1620 |
| ccaccagagg aaattgcaat gctagaaaaa atagtgccag aggtgatgga aaacgctatt | 1680 |
| aaactgattg tacctttgaa agtggattat gcctttggtt catcttggta tgacacgaag | 1740 |
| tag | 1743 |

<210> SEQ ID NO 4
<211> LENGTH: 877
<212> TYPE: PRT
<213> ORGANISM: Psychrobacillus sp.

<400> SEQUENCE: 4

```
Met Tyr Leu Ser Thr Glu Lys Ile Leu Leu Asp Gly Asn Ser Leu
1               5                   10                  15

Ala Tyr Arg Ala Phe Phe Ala Leu Pro Leu Leu Thr Asn Glu His Gly
            20                  25                  30

Ile His Thr Asn Ala Val Tyr Gly Phe Thr Met Met Leu Gln Lys Ile
        35                  40                  45

Met Asp Glu Glu Asn Pro Thr His Met Leu Val Ala Phe Asp Ala Gly
    50                  55                  60

Lys Thr Thr Phe Arg His Ser Thr Phe Gly Asp Tyr Lys Gly Gly Arg
65                  70                  75                  80

Gln Lys Thr Pro Pro Glu Leu Ser Glu Gln Phe Pro Tyr Ile Arg Lys
                85                  90                  95

Leu Ile Asp Ala Tyr Gly Ile Lys Arg Tyr Glu Leu Glu Met Tyr Glu
            100                 105                 110

Ala Asp Asp Ile Ile Gly Thr Leu Ser Lys Arg Ala Asp Glu Lys Gly
        115                 120                 125

Gln Gln Val Val Ile Val Ser Gly Asp Lys Asp Leu Thr Gln Leu Ala
    130                 135                 140

Thr Asp Lys Thr Thr Val Tyr Ile Thr Arg Lys Gly Ile Thr Asp Ile
145                 150                 155                 160

Glu Lys Tyr Thr Pro Glu His Val Gln Glu Lys Tyr Gly Leu Thr Pro
                165                 170                 175

Leu Gln Ile Ile Asp Met Lys Gly Leu Met Gly Asp Ala Ser Asp Asn
            180                 185                 190

Ile Pro Gly Val Pro Gly Val Gly Glu Lys Thr Ala Ile Lys Leu Leu
        195                 200                 205

Lys Glu His Gly Ser Val Glu Asp Leu Tyr Lys Ala Leu Asp Thr Val
    210                 215                 220

Ser Gly Val Lys Leu Lys Glu Lys Leu Ile Ala Asn Glu Glu Gln Ala
225                 230                 235                 240

Ile Met Ser Lys Ala Leu Ala Thr Ile Glu Thr Ala Ala Pro Ile Gln
                245                 250                 255

Ile Ser Ile Asp Asp Leu Ser Tyr Thr Gly Pro Asn Met Glu Glu Val
            260                 265                 270

Ile Glu Val Trp Lys Glu Leu Ala Phe Lys Thr Leu Leu Glu Lys Ser
        275                 280                 285

Asp Tyr Ile Ser Glu Glu Ser Gly Thr Thr Glu Val Ala Phe Glu Ile
    290                 295                 300
```

```
Val Glu Glu Ile Asp Ser Thr Ile Leu Asp Lys Val Met Ser Val His
305                 310                 315                 320

Leu Glu Met Tyr Asp Gly Gln Tyr His Thr Ser Glu Leu Leu Gly Ile
            325                 330                 335

Ala Leu Ser Asp Gly Glu Lys Gly Tyr Phe Ala Pro Ala Asp Ile Ala
            340                 345                 350

Phe Gln Ser Lys Asp Phe Cys Ser Trp Leu Glu Asn Ala Thr Asn Lys
            355                 360                 365

Lys Tyr Leu Ala Asp Ser Lys Ala Thr Gln Ala Val Ser Arg Lys His
        370                 375                 380

Asn Val Asn Val His Gly Val Glu Phe Asp Leu Leu Ala Ala Tyr
385                 390                 395                 400

Ile Val Asn Pro Ala Ile Ser Ser Glu Asp Val Ala Ala Ile Ala Lys
                405                 410                 415

Glu Phe Gly Tyr Phe Asn Leu Leu Thr Asn Asp Ser Val Tyr Gly Lys
            420                 425                 430

Gly Ala Lys Lys Thr Ala Pro Glu Ile Glu Lys Ile Ala Glu His Ala
        435                 440                 445

Val Arg Lys Ala Arg Ala Ile Trp Asp Leu Lys Glu Lys Leu Glu Val
450                 455                 460

Lys Leu Glu Glu Asn Glu Gln Tyr Ala Leu Tyr Lys Glu Ile Glu Leu
465                 470                 475                 480

Pro Leu Ala Ser Ile Leu Gly Thr Met Glu Ser Asp Gly Val Leu Val
                485                 490                 495

Asp Lys Gln Ile Leu Val Glu Met Gly His Glu Leu Asn Ile Lys Leu
            500                 505                 510

Arg Ala Ile Glu Gln Asp Ile Tyr Ala Leu Ala Gly Glu Thr Phe Asn
        515                 520                 525

Ile Asn Ser Pro Lys Gln Leu Gly Val Ile Leu Phe Glu Lys Ile Gly
        530                 535                 540

Leu Thr Pro Ile Lys Lys Thr Lys Thr Gly Tyr Ser Thr Ala Ala Asp
545                 550                 555                 560

Val Leu Glu Lys Leu Ala Ser Glu His Glu Ile Ile Glu Gln Ile Leu
                565                 570                 575

Leu Tyr Arg Gln Leu Gly Lys Leu Asn Ser Thr Tyr Ile Glu Gly Leu
            580                 585                 590

Leu Lys Glu Ile His Glu Asp Asp Gly Lys Ile His Thr Arg Tyr Gln
        595                 600                 605

Gln Ala Leu Thr Ser Thr Gly Arg Leu Ser Ser Ile Asn Pro Asn Leu
        610                 615                 620

Gln Asn Ile Pro Val Arg Leu Glu Glu Gly Arg Lys Ile Arg Lys Ala
625                 630                 635                 640

Phe Val Pro Ser Gln Pro Gly Trp Val Met Phe Ala Ala Asp Tyr Ser
                645                 650                 655

Gln Ile Glu Leu Arg Val Leu Ala His Met Ser Glu Asp Glu Asn Leu
            660                 665                 670

Val Glu Ala Phe Asn Asn Asp Leu Asp Ile His Thr Lys Thr Ala Met
        675                 680                 685

Asp Val Phe His Val Glu Gln Glu Ala Val Thr Ser Asp Met Arg Arg
        690                 695                 700

Ala Ala Lys Ala Val Asn Phe Gly Ile Val Tyr Gly Ile Ser Asp Tyr
705                 710                 715                 720

Gly Leu Ser Gln Asn Leu Asp Ile Thr Arg Lys Glu Ala Ala Thr Phe
```

```
                725                 730                 735
Ile Glu Asn Tyr Leu Asn Ser Phe Pro Gly Val Lys Gly Tyr Met Asp
                    740                 745                 750

Asp Ile Val Gln Asp Ala Lys Gln Thr Gly Tyr Val Thr Thr Ile Leu
        755                 760                 765

Asn Arg Arg Tyr Leu Pro Glu Ile Thr Ser Ser Asn Phe Asn Leu
770                 775                 780

Arg Ser Phe Ala Glu Arg Thr Ala Met Asn Thr Pro Ile Gln Gly Ser
785                 790                 795                 800

Ala Ala Asp Ile Ile Lys Lys Ala Met Ile Asp Met Ala Glu Arg Leu
            805                 810                 815

Ile Ser Glu Asn Met Gln Thr Lys Met Leu Leu Gln Val His Asp Glu
                820                 825                 830

Leu Ile Phe Glu Ala Pro Pro Glu Glu Ile Ala Met Leu Glu Lys Ile
            835                 840                 845

Val Pro Glu Val Met Glu Asn Ala Ile Lys Leu Ile Val Pro Leu Lys
        850                 855                 860

Val Asp Tyr Ala Phe Gly Ser Ser Trp Tyr Asp Thr Lys
865                 870                 875

<210> SEQ ID NO 5
<211> LENGTH: 2634
<212> TYPE: DNA
<213> ORGANISM: Psychrobacillus sp.

<400> SEQUENCE: 5
atgtatttgt caaccgagaa atcctatta ttagacggca atagtttggc ataccgagct      60
ttttttgccc taccttttatt aacaaatgaa catggaatac atacaaacgc agtatatggc    120
tttacaatga tgctacaaaa aattatggat gaagaaaatc ctactcatat gctcgtggca    180
tttgatgccg ggaaaacgac cttccgtcac tctacttttg gggattataa aggtggaaga    240
caaaaaacac caccagaact atcggaacaa ttcccttata tacgcaagtt aatcgatgct    300
tatggtatta gcgatacga actggaaatg tacgaagcag acgatattat cggtactta    360 agcaagcgtg cagacgaaaa agggcagcaa gttgtaattg tctcaggtga taaagattta    420
acacaactag ctacagataa aacaactgtg tatatcacaa gaaaaggcat aaccgatatt    480 gaaaatata cacctgaaca tgtacaagaa agtatggct taactccatt acagattata    540
gacatgaaag gtttaatggg agatgcttct gataatattc caggagttcc tggtgtcgga    600
gaaaaaacag ctattaagct ttttaaaaga catggttcgg tagaggattt atataaagca    660
cttgatacag ttagtggtgt taaactaaag gaaaaactca tcgccaacga agagcaggca    720
attatgagta aggcattagc tacgattgaa acagctgcac cgatacagat ttctatagac    780 gatcttcat atactggtcc taatatggaa gaagtaattg aagtttggaa ggaactagct    840
tttaaaactc ttcttgagaa atctgactat atttctgagg aatccgaaac tacagaagta    900
gcattcgaga ttgttgaaga aattgactct acaatattag ataaagtaat gtcagtccat    960
ttagaaatgt atgatgggca atatcataca agcgaattat taggtattgc ttttatcagat   1020 ggagaaaagg gttattttgc tcctgctgat atagcttttc aatcgaagga tttttgttct   1080
tggttagaaa atgctacgaa taaaaagtat ttagcagact ccaaagcaac acaagcagtg    1140
agtagaaaac ataatgtgaa tgtacatgga gtggaattcg accttctttt agcagcgtat    1200
atagtaaatc ctgctatctc ttcagaggat gttgctgcta ttgctaaaga atttggatat   1260
```

```
tttaacttgc tgacaaacga tagtgtttat gggaaaggtg ccaaaaaaac cgcacctgaa    1320
atcgagaaaa ttgcagaaca tgccgtaaga aaagcaaggg ctatttggga cttgaaagaa    1380
aagttagaag taaaactgga agaaaatgaa caatatgcgt tgtataaaga aatagagcta    1440
ccgcttgcat ctatccttgg tacgatgaaa tcagatgggg tgctggtgga taaacaaatt    1500
cttgtagaaa tgggtcatga gcttaatatt aagttacgag cgattgaaca agacatttat    1560
gcgttagctg gtgaaacgtt taatattaat tcacctaaac aattaggtgt aatactattt    1620
gaaaaaattg gtcttacccc tattaaaaag acaaaaacgg gctattcaac tgcagcagat    1680
gttttggaaa aactagcaag tgaacatgaa ataatagagc aaattttact atatcgtcaa    1740
ttaggtaaac tcaattccac atatatcgaa ggattattaa aagagattca tgaagatgat    1800
gggaagatcc ataccccgata tcaacaagcc ctaacttcaa ctgggcgttt gagttcgatc    1860
aatccaaacc ttcaaaatat accagttcgt ttagaagaag gtagaaaaat acgtaaagcc    1920
tttgttcctt cacaaccggg atgggtaatg tttgcggcgg attactctca aattgaattg    1980
cgtgttcttg cccatatgtc tgaggatgaa aacctggtag aagcttttaa taatgatctg    2040
gatattcata ctaaaacggc tatggatgta ttccatgtgg agcaggaagc agtaacgtcc    2100
gatatgcgcc gtgctgctaa ggcagttaac tttgggattg tgtatggtat tagtgattat    2160
ggtttatcac aaaacctaga tattactaga aaagaagcgg cgacatttat cgagaattat    2220
ttaaatagct tcccaggtgt aaaaggatat atggatgata tcgttcaaga tgcgaaacaa    2280
acaggctacg ttacaacaat tttgaataga cgaagatatt tgcctgaaat aacaagttct    2340
aactttaatc tccgcagttt tgcagaacgt actgctatga atacaccaat tcaagggagt    2400
gcagccgata ttattaaaaa agcaatgatc gatatggcgg aaagattaat atcagaaaat    2460
atgcagacca aaatgctact acaagtacat gatgaattaa tttttgaggc tccaccagag    2520
gaaattgcaa tgctagaaaa aatagtgcca gaggtgatgg aaaacgctat taaactgatt    2580
gtacctttga aagtggatta tgcctttggt tcatcttggt atgacacgaa gtag          2634
```

<210> SEQ ID NO 6
<211> LENGTH: 32
<212> TYPE: PRT
<213> ORGANISM: Bacillus species C3_41

<400> SEQUENCE: 6

Met Arg Arg Ala Ala Lys Ala Val Asn Phe Gly Ile Val Tyr Gly Ile
1               5                   10                  15

Ser Asp Tyr Gly Leu Ser Gln Asn Leu Asp Ile Thr Arg Lys Glu Ala
            20                  25                  30

<210> SEQ ID NO 7
<211> LENGTH: 32
<212> TYPE: PRT
<213> ORGANISM: Ureibacillus thermosphaericus

<400> SEQUENCE: 7

Met Arg Arg Ala Ala Lys Ala Val Asn Phe Gly Ile Ile Tyr Gly Ile
1               5                   10                  15

Ser Asp Tyr Gly Leu Ser Gln Asn Leu Asp Ile Ser Arg Lys Glu Ala
            20                  25                  30

<210> SEQ ID NO 8
<211> LENGTH: 32
<212> TYPE: PRT
<213> ORGANISM: Bacillus subtilis -continued

```
<400> SEQUENCE: 8

Met Arg Arg Gln Ala Lys Ala Val Asn Phe Gly Ile Val Tyr Gly Ile
1               5                   10                  15

Ser Asp Tyr Gly Leu Ser Gln Asn Leu Gly Ile Thr Arg Lys Glu Ala
            20                  25                  30

<210> SEQ ID NO 9
<211> LENGTH: 32
<212> TYPE: PRT
<213> ORGANISM: Bacillus smithii

<400> SEQUENCE: 9

Met Arg Arg Gln Ala Lys Ala Val Asn Phe Gly Ile Val Tyr Gly Ile
1               5                   10                  15

Ser Asp Tyr Gly Leu Ser Gln Asn Leu Gly Ile Thr Arg Lys Glu Ala
            20                  25                  30

<210> SEQ ID NO 10
<211> LENGTH: 32
<212> TYPE: PRT
<213> ORGANISM: Geobacillus stearothermophilus

<400> SEQUENCE: 10

Met Arg Arg Gln Ala Lys Ala Val Asn Phe Gly Ile Val Tyr Gly Ile
1               5                   10                  15

Ser Asp Tyr Gly Leu Ala Gln Asn Leu Asn Ile Ser Arg Lys Glu Ala
            20                  25                  30

<210> SEQ ID NO 11
<211> LENGTH: 580
<212> TYPE: PRT
<213> ORGANISM: Geobacillus stearothermophilus

<400> SEQUENCE: 11

Ala Lys Met Ala Phe Thr Leu Ala Asp Arg Val Thr Glu Glu Met Leu
1               5                   10                  15

Ala Asp Lys Ala Ala Leu Val Val Glu Val Val Glu Glu Asn Tyr His
            20                  25                  30

Asp Ala Pro Ile Val Gly Ile Ala Val Val Asn Glu His Gly Arg Phe
        35                  40                  45

Phe Leu Arg Pro Glu Thr Ala Leu Ala Asp Pro Gln Phe Val Ala Trp
    50                  55                  60

Leu Gly Asp Glu Thr Lys Lys Lys Ser Met Phe Asp Ser Lys Arg Ala
65                  70                  75                  80

Ala Val Ala Leu Lys Trp Lys Gly Ile Glu Leu Cys Gly Val Ser Phe
                85                  90                  95

Asp Leu Leu Leu Ala Ala Tyr Leu Leu Asp Pro Ala Gln Gly Val Asp
            100                 105                 110

Asp Val Ala Ala Ala Lys Met Lys Gln Tyr Glu Ala Val Arg Pro
        115                 120                 125

Asp Glu Ala Val Tyr Gly Lys Gly Ala Lys Arg Ala Val Pro Asp Glu
    130                 135                 140

Pro Val Leu Ala Glu His Leu Val Arg Lys Ala Ala Ile Trp Glu
145                 150                 155                 160

Leu Glu Arg Pro Phe Leu Asp Glu Leu Arg Arg Asn Glu Gln Asp Arg
                165                 170                 175

Leu Leu Val Glu Leu Glu Gln Pro Leu Ser Ser Ile Leu Ala Glu Met
```

```
                180             185             190
Glu Phe Ala Gly Val Lys Val Asp Thr Lys Arg Leu Glu Gln Met Gly
            195                 200                 205
Lys Glu Leu Ala Glu Gln Leu Gly Thr Val Glu Gln Arg Ile Tyr Glu
        210                 215                 220
Leu Ala Gly Gln Glu Phe Asn Ile Asn Ser Pro Lys Gln Leu Gly Val
225                 230                 235                 240
Ile Leu Phe Glu Lys Leu Gln Leu Pro Val Leu Lys Lys Thr Lys Thr
                245                 250                 255
Gly Tyr Ser Thr Ser Ala Asp Val Leu Glu Lys Leu Ala Pro Tyr His
            260                 265                 270
Glu Ile Val Glu Asn Ile Leu His Tyr Arg Gln Leu Gly Lys Leu Gln
        275                 280                 285
Ser Thr Tyr Ile Glu Gly Leu Leu Lys Val Val Arg Pro Asp Thr Lys
290                 295                 300
Lys Val His Thr Ile Phe Asn Gln Ala Leu Thr Gln Thr Gly Arg Leu
305                 310                 315                 320
Ser Ser Thr Glu Pro Asn Leu Gln Asn Ile Pro Ile Arg Leu Glu Glu
                325                 330                 335
Gly Arg Lys Ile Arg Gln Ala Phe Val Pro Ser Glu Ser Asp Trp Leu
            340                 345                 350
Ile Phe Ala Ala Asp Tyr Ser Gln Ile Glu Leu Arg Val Leu Ala His
        355                 360                 365
Ile Ala Glu Asp Asp Asn Leu Met Glu Ala Phe Arg Arg Asp Leu Asp
370                 375                 380
Ile His Thr Lys Thr Ala Met Asp Ile Phe Gln Val Ser Glu Asp Glu
385                 390                 395                 400
Val Thr Pro Asn Met Arg Arg Gln Ala Lys Ala Val Asn Phe Gly Ile
                405                 410                 415
Val Tyr Gly Ile Ser Asp Tyr Gly Leu Ala Gln Asn Leu Asn Ile Ser
            420                 425                 430
Arg Lys Glu Ala Ala Glu Phe Ile Glu Arg Tyr Phe Glu Ser Phe Pro
        435                 440                 445
Gly Val Lys Arg Tyr Met Glu Asn Ile Val Gln Glu Ala Lys Gln Lys
        450                 455                 460
Gly Tyr Val Thr Thr Leu Leu His Arg Arg Arg Tyr Leu Pro Asp Ile
465                 470                 475                 480
Thr Ser Arg Asn Phe Asn Val Arg Ser Phe Ala Glu Arg Met Ala Met
                485                 490                 495
Asn Thr Pro Ile Gln Gly Ser Ala Ala Asp Ile Ile Lys Lys Ala Met
            500                 505                 510
Ile Asp Leu Asn Ala Arg Leu Lys Glu Glu Arg Leu Gln Ala His Leu
        515                 520                 525
Leu Leu Gln Val His Asp Glu Leu Ile Leu Glu Ala Pro Lys Glu Glu
        530                 535                 540
Met Glu Arg Leu Cys Arg Leu Val Pro Glu Val Met Glu Gln Ala Val
545                 550                 555                 560
Thr Leu Arg Val Pro Leu Lys Val Asp Tyr His Tyr Gly Ser Thr Trp
                565                 570                 575
Tyr Asp Ala Lys
            580

<210> SEQ ID NO 12
```

```
<211> LENGTH: 580
<212> TYPE: PRT
<213> ORGANISM: Ureibacillus thermosphaericus

<400> SEQUENCE: 12

Ala Ala Leu Ser Phe Lys Ile Val Arg Glu Ile Ala Glu Asp Leu Phe
1               5                   10                  15

Thr Asp Thr Met Ala Val His Val Glu Leu Glu Asn Glu His Tyr His
            20                  25                  30

Thr Cys Asn Ile Leu Gly Phe Gly Phe Thr Asp Gly Ser Asn Thr Phe
        35                  40                  45

Phe Val Pro Thr Glu Val Leu Gln Lys Ser Glu Arg Leu Lys Ser Tyr
    50                  55                  60

Phe Glu Asp Glu Thr Lys Lys Lys Tyr Met Ser Asp Leu Lys Ala Ala
65                  70                  75                  80

Gln Cys Ile Leu Lys Arg His Gly Ile Asn Leu Arg Gly Val Glu Phe
                85                  90                  95

Asp Leu Leu Leu Ala Ser Tyr Ile Val Asn Pro Ala Ile Ser Gly Asp
            100                 105                 110

Asp Val Ala Thr Leu Ala Lys Glu Phe Gly Tyr Thr Asp Val Arg Ser
        115                 120                 125

Asn Glu Ala Val Tyr Gly Lys Gly Ala Lys Trp Ala Leu Pro Ser Glu
    130                 135                 140

Glu Val Leu Ala Glu His Val Cys Arg Lys Ala Phe Ala Ile Trp Ser
145                 150                 155                 160

Cys Lys Glu Arg Val Ser Asn Lys Leu Lys Glu Asn Glu Gln Phe Asp
                165                 170                 175

Leu Tyr His Asp Leu Glu Leu Pro Leu Ala Val Ile Leu Gly Lys Met
            180                 185                 190

Glu Ser Glu Gly Ile Lys Val Asn Ile Ser Thr Leu Glu Thr Met Gly
        195                 200                 205

Gln Glu Leu Glu Asp Lys Ile Ala Lys Leu Glu Thr Glu Ile Tyr Glu
    210                 215                 220

Leu Ala Gly Glu Thr Phe Asn Ile Asn Ser Pro Lys Gln Leu Gly Val
225                 230                 235                 240

Ile Leu Phe Glu Lys Leu Gly Leu Pro Val Ile Lys Lys Thr Lys Thr
                245                 250                 255

Gly Tyr Ser Thr Ala Ala Asp Val Leu Glu Lys Leu Lys Ser Glu His
            260                 265                 270

Gln Ile Val Gln Leu Ile Leu Glu Tyr Arg Thr Leu Ala Lys Leu Gln
        275                 280                 285

Ser Thr Tyr Ile Glu Gly Leu Ile Lys Glu Val His Pro Lys Asp Ser
    290                 295                 300

Lys Val His Thr Arg Phe Met Gln Ala Leu Thr Ser Thr Gly Arg Leu
305                 310                 315                 320

Ser Ser Thr Asp Pro Asn Leu Gln Asn Ile Pro Ile Arg Leu Glu Glu
                325                 330                 335

Gly Arg Lys Ile Arg Lys Ala Phe Val Pro Ser His Asp Gly Trp Leu
            340                 345                 350

Leu Phe Ser Ala Asp Tyr Ser Gln Ile Glu Leu Arg Val Leu Ala His
        355                 360                 365

Met Ser Lys Asp Lys Asn Leu Val Glu Ala Phe Asn Gln Gly Met Asp
    370                 375                 380

Ile His Thr Arg Thr Ala Met Glu Val Phe His Val Ser Gln Asp Asp
```

```
                385                 390                 395                 400
        Val Thr Ser Asn Met Arg Arg Ala Ala Lys Ala Val Asn Phe Gly Ile
                        405                 410                 415
        Ile Tyr Gly Ile Ser Asp Tyr Gly Leu Ser Gln Asn Leu Asp Ile Ser
                        420                 425                 430
        Arg Lys Glu Ala Gly Glu Phe Ile Glu Lys Tyr Phe Glu Ser Phe Pro
                        435                 440                 445
        Gly Val Lys Glu Tyr Met Asp Asn Ile Val Gln Glu Ala Lys Leu Lys
                        450                 455                 460
        Gly Tyr Val Thr Thr Ile Leu Asn Arg Arg Tyr Leu Pro Asp Ile
        465                 470                 475                 480
        Thr Ser Lys Asn Phe Asn Leu Arg Ser Phe Ala Glu Arg Thr Ala Met
                        485                 490                 495
        Asn Thr Pro Ile Gln Gly Ser Ala Ala Asp Ile Ile Lys Lys Ala Met
                        500                 505                 510
        Leu Asp Ile Asp Ala Arg Leu Asn Ser Glu Gly Leu Gln Ala Lys Leu
                        515                 520                 525
        Leu Leu Gln Val His Asp Glu Leu Ile Phe Glu Ala Pro Lys Glu Glu
                        530                 535                 540
        Ile Glu Lys Leu Glu Lys Ile Val Pro Glu Val Met Glu Ser Ala Ile
        545                 550                 555                 560
        Leu Leu Asp Val Pro Leu Lys Val Asp Ile Ser Tyr Gly Glu Thr Trp
                        565                 570                 575
        Tyr Asp Ala Lys
                    580

<210> SEQ ID NO 13
<211> LENGTH: 1743
<212> TYPE: DNA
<213> ORGANISM: Artificial Sequence
<220> FEATURE:
<223> OTHER INFORMATION: Synthetic

<400> SEQUENCE: 13
accgaagttg catttgaaat tgtggaagaa atcgatagca ccatcctgga taaagttatg      60
agcgttcatc tggaaatgta tgatggtcag tatcatacca gcgaactgct gggtattgca     120
ctgagtgatg tgaaaaaggt tattttgca ccggcagata ttgcctttca gagcaaagat     180
ttttgtagct ggctggaaaa tgccaccaac aaaaaatacc tggcagatag caaagcaacc     240
caggcagtta gccgtaaaca taatgttaat gttcacggcg tggaatttga tctgctgctg     300
gcagcatata ttgttaatcc ggcaattagc agcgaagatg ttgcagcaat tgcaaaagaa     360
ttcggctatt ttaacctgct gaccaacgat agcgtttatg gtaaaggtgc aaaaaaaacc     420
gcaccggaaa ttgaaaaaat gccgaacat gcagttcgta aagcacgtgc aatttgggat     480
ctgaaagaaa aactggaagt gaaactggaa gagaacgaac agtatgccct gtataaagaa     540
attgaactgc cgctggcaag cattctgggc accatggaaa tgatggtgt tctggttgat     600 aaacaaatcc tggttgaaat gggtcacgag ctgaacatta aactgcgtgc aattgaacag     660
gatatttatg cactggcagg cgaaaccttt aacattaata gcccgaaaca gctgggtgtg     720
atcctgtttg aaaaaatcgg tctgacccg atcaaaaaaa ccaaaaccgg ttatagcacc     780
gcagcagatg ttctggaaaa actggcaagc gaacatgaaa ttattgagca gattctgctg     840
tatcgtcagc tgggtaaact gaatagcacc tatattgaag gtctgctgaa agaaatccat     900
gaggatgatg gtaaaatcca taccgttat cagcaggcac tgaccagcac cggtcgtctg     960
```

```
agcagcatta atccgaatct gcagaatatt ccggttcgtc tggaagaagg tcgtaaaatt    1020
cgtaaagcat ttgttccgag ccagcctggt tgggttatgt ttgcagcaga ttatagccag    1080
attgaactgc gtgttctggc acatatgagc gaagatgaaa atctggttga agcctttaac    1140
aacgatctgg atattcatac caaaaccgcc atggatgttt ttcacgttga acaagaagca    1200
gttaccagcg atatgcgtcg tgcagcaaaa gcagttaatt ttggtattgt gtatggcatc    1260
agcgcttatg gtctgagcca gaatctggat attacccgta aagaagcagc caccttatc     1320 gaaaactacc tgaatagctt tccgggtgtg aaaggctata tggatgatat tgttcaggat    1380
gcaaaacaga ccggttatgt taccaccatt ctgaatcgtc gtcgttatct gccggaaatt    1440
accagcagca actttaatct gcgtagcttt gcagaacgta ccgcaatgaa tacccccgatt   1500 cagggtagcg cagcagatat tatcaaaaaa gccatgattg atatggccga acgtctgatt   1560
agcgaaaata tgcagaccaa atgctgctg caggttcatg atgaactgat tttttgaagca   1620 ccgcctgaag aaattgcaat gctggaaaaa attgttccgg aagtgatgga aaacgccatt    1680
aaactgattg ttccgctgaa agtggattat gcatttggta gcagttggta cgataccaaa    1740
taa                                                                  1743

<210> SEQ ID NO 14
<211> LENGTH: 1743
<212> TYPE: DNA
<213> ORGANISM: Artificial Sequence
<220> FEATURE:
<223> OTHER INFORMATION: Synthetic

<400> SEQUENCE: 14
gccaaaatgg catttaccct ggcagatcgt gttaccgaag aaatgctggc agataaagca      60
gcactggttg ttgaagttgt ggaagaaaat tatcatgatg caccgattgt tggtattgcc     120
gttgttaatg aacatggccg tttttttctg cgtccggaaa ccgcactggc cgatccgcag     180
tttgttgcat ggctgggtga tgaaaccaaa aaaagagca tgtttgatag caaacgtgca     240
gcagttgcac tgaaatggaa aggtattgaa ctgtgcggtg tttcatttga tctgctgctg     300
gcagcatatc tgctggatcc ggcacagggt gttgatgatg ttgcagcagc agcaaagatg     360
aaacagtatg aagcagttcg tccggatgaa gccgtttatg gtaaaggtgc aaaacgtgcc     420
gtgccggatg aaccggtgct ggccgaacat ctggttcgta aagcagccgc aatttgggaa     480
ttagaacgtc cgtttctgga tgaactgcgt cgtaatgaac aggatcgtct gctggttgaa     540
ctggaacagc cgctgagcag cattctggca gaaatggaat ttgccggtgt taaagtggat    600
accaaacgtc tggaacaaat gggtaaagaa ctggcagaac agctgggcac cgttgaacag    660
cgtatttatg agctggcagg tcaagaattt aacatcaata gcccgaaaca actgggcgtg    720
attctgtttg aaaaactgca gctgccggtt ctgaaaaaaa ccaaaaccgg ttatagcacc    780
agcgcagatg ttctggaaaa actggcaccg tatcatgaaa ttgtggaaaa cattctgcat    840
tatcgccagc tgggtaaact gcagagcacc tatattgaag gtctgctgaa agttgttcgt    900
cccgatacca aaaagtgca caccatttt aaccaggcac tgacccagac cggtcgtctg      960
agcagtaccg aaccgaatct gcagaatatt ccgattcgtc tggaagaagg tcgtaaaatt    1020
cgtcaggcct ttgttccgag cgaaagcgat tggctgattt ttgcagcaga ttatagccag    1080
attgaactgc gcgttctggc acatattgcc gaagatgata atctgatgga agcatttcgt    1140
cgcgatctgg atattcatac caaaacagcc atggatattt ttcaggtgag cgaagatgaa    1200
```

```
gttaccccga atatgcgtcg tcaggcaaaa gcagttaatt ttggtattgt gtatggcatt    1260
agcgcatatg gtctggcaca gaatctgaat attagccgta aagaagcagc cgagtttatc    1320
gaacgttatt ttgaaagttt tccgggtgtg aaacgctata tggaaaatat tgttcaagaa    1380
gccaaacaga aaggctatgt taccacactg ctgcatcgtc gtcgttatct gccggatatt    1440
accagccgta actttaatgt tcgtagcttt gcagaacgta tggcaatgaa taccccgatt    1500
cagggtagcg cagccgatat tatcaaaaaa gcaatgattg atctgaacgc acgcctgaaa    1560
gaagaacgtc tgcaggcaca tctgctgtta caggttcatg atgaactgat tctggaagcc    1620
cctaaagaag agatggaacg tctttgtcgt ctggttccgg aagttatgga acaggcagtt    1680
accctgcgtg ttccgctgaa agtggattat cattatggta gcacctggta tgatgccaaa    1740
taa                                                                  1743

<210> SEQ ID NO 15
<211> LENGTH: 1743
<212> TYPE: DNA
<213> ORGANISM: Artificial Sequence
<220> FEATURE:
<223> OTHER INFORMATION: Synthetic

<400> SEQUENCE: 15
gcagcactga gctttaaaat cgttcgtgaa attgcagagg acctgtttac cgataccatg      60
gcagttcatg ttgaactgga aaacgaacat tatcacacgt gcaacattct tggttttggt     120
tttaccgatg gcagcaacac ctttttttgtt ccgaccgaag tgctgcagaa aagcgaacgt    180
ctgaaaagct attttgagga tgaaaccaaa aaaaagtata tgagcgatct gaaagcagcc    240
cagtgtattc tgaaacgtca tggtattaat ctgcgtggcg ttgaatttga tctgctgctg    300
gcaagctata ttgttaatcc ggcaattagc ggtgatgatg ttgcacccct ggcaaaagaa    360
tttggctata ccgatgttcg tagcaatgaa gccgtttatg gtaaaggtgc aaaatgggca    420
ctgccgagcg aagaggttct ggcagaacat gtttgtcgta agcatttgc aatttggagc     480 tgcaaagaac gcgttagcaa taaactgaaa gagaacgaac agttcgatct gtatcatgat    540
ctggaactgc cgctggccgt tattctgggt aaaatggaaa gcgaaggcat caaagtgaat    600
atcagcaccc tggaaaccat gggtcaagaa ctggaagata aaattgccaa actggaaacc    660
gagatctatg aactggcagg cgaaaccttt aacattaata gcccgaaaca gctgggtgtg    720
atcctgtttg aaaaactggg tctgccggtt atcaaaaaaa cgaaaaccgg ttatagcacc    780
gcagcagatg ttctggaaaa actgaaatca gaacatcaga ttgtgcagct gattctggaa    840
tatcgtaccc tggccaaact gcagagcacc tatattgaag gtctgatcaa agaagtgcat    900
ccgaaagata gcaaagtgca tacccgtttt atgcaggcac tgaccagcac cggtcgtctg    960
agcagcaccg atccgaatct gcagaatatt ccgattcgtc tggaagaagg tcgtaaaatt   1020
cgcaaagcct ttgtgccgag ccatgatggt tggctgctgt ttagcgcaga ttatagccag   1080
attgaactgc gtgttctggc acatatgagc aaagataaaa atctggtgga agcctttaac   1140
caaggcatgg atattcatac ccgtaccgca atggaagttt ttcatgttag ccaggatgat   1200
gtgaccagca atatgcgtcg tgcagcaaaa gcagttaatt tcgtattat ctatggcatt    1260 agcgcatatg gtctgagcca gaatctggat atttcacgta aagaagcagg cgaattcatc   1320
gagaaatact ttgaaagttt tccgggtgtg aaagaatata tggacaacat tgttcaagag   1380
gccaagctga aaggttatgt taccaccatt ctgaatcgtc gtcgttatct gccggatatt   1440
accagcaaaa atttcaatct gcgtagcttt gcagaacgta ccgccatgaa taccccgatt    1500
```

-continued

```
cagggtagcg cagccgatat catcaaaaaa gcaatgctgg atattgatgc ccgtctgaat    1560
agcgaaggtc tgcaggcaaa actgctgctg caggttcacg atgaactgat ttttgaagca    1620
ccgaaagaag agatcgagaa gctggaaaaa attgttccgg aagttatgga aagtgccatt    1680
ctgctggatt ttccgctgaa agttgatatt agctatggtg aaacctggta cgatgccaaa    1740
taa                                                                  1743
```

<210> SEQ ID NO 16
<211> LENGTH: 82
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: labelled with the fluorophore Dabcyl
<220> FEATURE:
<221> NAME/KEY: misc_feature
<222> LOCATION: (32)..(32)
<223> OTHER INFORMATION: labelled with the fluorophore FAM

<400> SEQUENCE: 16

```
ggcccgtagg aggaaaggac atcttctagc atacgggccg tcaagttcat ggccagtcaa    60
gtcgtcagaa atttcgcacc ac                                             82
```

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17

```
gtggtgcgaa atttctgac                                                 19
```

<210> SEQ ID NO 18
<211> LENGTH: 19
<212> TYPE: DNA
<213> ORGANISM: Artificial Sequence
<220> FEATURE:
<223> OTHER INFORMATION: Synthetic

<400> SEQUENCE: 18

```
tatccaccaa tactaccct                                                 19
```

<210> SEQ ID NO 19
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: labelled at 3' end with TAMRA fluorophore

<400> SEQUENCE: 19

```
cgatactttg tccactcaat                                                20
```

<210> SEQ ID NO 20
<211> LENGTH: 40
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (1)..(1)
<223> OTHER INFORMATION: labelled at 5' end with Black Hole Quencher 2

<400> SEQUENCE: 20
attgagtgga caaagtatcg tagggtagta ttggtggata                              40
```

DNA POLYMERASES

CROSS-REFERENCE TO RELATED APPLICATIONS

This application is a U.S. National Stage Application of PCT/EP2018/085342, filed on Dec. 17, 2018, which claims the benefit of GB 1721053.5, filed on Dec. 15, 2017, each of which is herein incorporated by reference in its entirety.

INCORPORATION OF SEQUENCE LISTING

This application contains a sequence listing submitted in Computer Readable Form (CRF) on Jun. 28, 2020. The paper copy of the sequence listing and the CRF are identical and are incorporated herein by reference. The sequence listing contains one file called "Sub-Sequence_Listing.txt" which is 38.6 kilobytes in size and which was created on Jun. 25, 2020.

The present invention relates to DNA polymerases. In particular, the present invention relates to modified DNA polymerases with enhanced strand displacement activity (SDA).

The gold standard of microbial identification still remains culturing and subsequent phenotypic differentiation of the causative agent, a process often taking several days to perform and analyze, and this delay may have major impact on morbidity and mortality of an infectious disease. In addition, many organisms cannot grow on culture media, hence, will be undetected by existing culturing methods.

There is a global need to monitor and diagnose critical infectious diseases such as HIV/AIDS, tuberculosis, malaria, cholera etc. The challenge becomes even more critical in potential epidemic situations such as Ebola, avian and swine influenza outbreaks. Despite advances in diagnostic technologies, many patients with suspected infections receive empiric antimicrobial therapy rather than appropriate therapy dictated by the rapid identification of the infectious agent. The result is overuse of our small inventory of effective antimicrobials whose numbers continue to dwindle due to antimicrobial resistance development. There is a clear demand for new and rapid on-site molecular diagnostic tests enabling identification of specific pathogens.

The Polymerase Chain Reaction (PCR) in many ways revolutionized the molecular genetics and diagnosis field. The workhorses in PCR technology, are thermostable high fidelity DNA polymerases which, together with cyclic events of heating and cooling to obtain strand separation, primer annealing and elongation, lead to amplification of a target DNA sequence. PCR technology is now widely employed in biomedical and life science research as well as molecular diagnostics.

Point-of-care (POC) diagnostics are described as medical tools or devices enabling disease diagnosis in a patient's community outside a hospital setting. The ideal diagnostic test should meet the "ASSURED" criteria: Affordable, Sensitive, Specific, User-friendly, Rapid and robust, Equipment-free and Delivered to those who need it. POC methods are preferably simple and do not require a heat source or stable power supply as these are typically not available at POC. Thus enzymes and reagents used should work at ambient temperatures.

Although PCR technology has a high potential, it still has strict limitations and requires the use of high precision electrically powered thermal cycling equipment for repeated heating and cooling processes and skilled personnel to run the equipment. Non-specific amplification due to spurious priming in the annealing process is problematic, and PCR is also prone to inhibitory compounds in "crude" samples. In addition, the bulky design of PCR devices make PCR an imperfect solution for incorporation into POC technology platforms and make PCR-based methods difficult to employ as the major technology driver in POC diagnostics.

Lately, an increased focus on non-PCR based methods, in particular Isothermal Amplification (IA) methods, has emerged. In these methods, nucleic acid amplification takes place at constant temperatures and has no need for high precision temperature cycling and control, or enzymes stable at high temperatures. Isothermal amplification methods are reported to have analytical sensitivities and specificities comparable to PCR as well as a higher tolerance to inhibitory compounds, while allowing shorter time to results and easier use. These features make isothermal amplification methods highly desirable for those developing POC molecular diagnostics platforms and aiming to meet "ASSURED" criteria. A number of different methods have in the last decade been published for isothermal amplification of nucleic acids (both RNA and DNA) (Reviewed by Gill, P. and A. Ghaemi (2008) *Nucleosides Nucleotides Nucleic Acids* 27(3): 224-243; Craw, P. and W. Balachandran (2012) *Lab Chip* 12(14): 2469-2486; de Paz, H. D. et al. (2014) *Expert Rev Mol Diagn* 14(7): 827-843; Yan, L. et al. (2014) *Mol Biosyst* 10(5): 970-1003 and new ones are continuously being developed (Liu, W. et al. (2015) Sci Reports 5: 12723). In several of the methods, success relies on the inherent strand displacement activity (SDA) of the DNA polymerase used in the reaction setup. The term strand displacement describes the ability of the polymerase to displace downstream DNA encountered during synthesis.

In addition to (POC) diagnostics also other areas of interest benefit from isothermal amplification technology empowered by the DNA polymerase. In this regard, whole genome amplification (multiple displacement amplification) is important especially when extremely limited amount of DNA is present such as in single cell approaches. Also, in next-generation sequencing approaches strand-displacing polymerases are important as exemplified by the Pacific Biosciences Single Molecule Real Time (SMRT) DNA sequencing technology and an isothermal amplification method for next generation sequencing published in 2013 by Ma et al. (Ma, Z. et al. *Proc Natl Acad Sci USA* 110(35): 14320-14323).

The current toolbox of polymerase enzymes which function well at ambient temperature is, however, very limited. Typically, different isothermal methods require reaction temperatures between 30-65° C. which are mainly determined by the working range of the polymerases used in the reactions and are prone to inhibition by salt.

A cold-adapted polymerase from a *Psychrobacillus* sp. (PB) belonging to the A-family of DNA polymerases has been characterized. This enzyme possesses high polymerase activity at ambient temperatures but still has good stability at elevated temperatures up to 40° C. Of particular interest, the marine derived enzyme also possesses good salt tolerance and strong strand-displacement activity (SDA) as well as proficient processivity at 25° C., and is comparable with the state-of-the art commercial enzymes (WO 2017/162765).

In many IA methods only a polymerase is required and the effectiveness of the method is heavily dependent on the SDA of that polymerase. Therefore anything which served to increase SDA of the PB or other polymerases used in IA would be highly desirable.

The present inventors have surprisingly found that a single point mutation in the finger domain of certain polymerases in the A family, in particular replacement of a single Asp residue, leads to significantly enhanced SDA.

Therefore, in a first aspect, the present invention provides a DNA polymerase, said DNA polymerase including the sequence of SEQ ID NO. 1 or a sequence which is at least 70%, preferably at least 75%, 78%, 80%, 82%, 85%, 88%, 90%, 92% or 95%, identical thereto, but wherein the aspartic acid residue at position 18 of SEQ ID NO. 1, or the equivalent aspartic acid residue in other sequences, has been replaced by a non-negatively charged amino acid residue.

SEQ ID NO. 1 is a fragment of the amino acid sequence of the PB polymerase I, it spans amino acids 405 to 436 in the truncated (lacking the 5'-3'-exonuclease domain) wild type PB sequence. This region (405-436) within the finger domain is highly conserved amongst some of the DNA polymerase A family (also known as pol I family), see FIGS. 1 and 5. DNA polymerases of the invention would typically be classed as of the DNA polymerase I or A type.

Preferred DNA polymerases of the invention comprise the sequence of SEQ ID NO. 6, 7, 8, 9 or 10 but wherein the aspartic acid residue at position 18 of each sequence has been replaced by a non-negatively charged amino acid residue.

In some embodiments, the DNA polymerase of the invention comprises an amino acid sequence that has single or multiple amino acid alterations (additions, substitutions, insertions or deletions) compared to SEQ ID NO:1. Such sequences preferably may contain up to 8, 7 or 6, e.g. only 1, 2, 3, 4 or 5, preferably 1, 2 or 3, more preferably 1 or 2, altered amino acids in addition to the replacement of the aforementioned Asp residue. Substitutions can be with conservative or non-conservative amino acids. Preferably said alterations are conservative amino acid substitutions.

A preferred polymerase of the invention is a modified PB polymerase, further preferred polymerases are modified polymerases from the species *Geobacillus stearothermophilus* (known as Bst), from *Bacillus subtilis* (known as Bsu), from *Bacillus smithii* (known as Bsm) and *Ureibacillus thermosphaericus* (known as Ubts).

The term "DNA polymerase" refers to an enzyme which catalyses the 5'→3' synthesis of DNA from individual nucleotides, the reaction being based on primer extension and standard Watson—Crick rules of base pairing to a template strand. Likewise, "DNA polymerase activity" refers to the 5'→3' synthesis of DNA from individual nucleotides, the reaction being based on primer extension and standard Watson—Crick rules of base pairing to a template strand. Enzymatically active (catalytically active) fragments of naturally occurring or modified polymerases are included within the term "DNA polymerase". The polymerase may also, but may not, have 3'→5' exonuclease and/or 5'→3' exonuclease activity. Preferably the DNA polymerases of the present invention lack 5'→3' exonuclease activity.

The present inventors have found that replacement of the aforementioned aspartic acid residue significantly increases SDA in several different DNA polymerases in the family known as DNA polymerase A, the enzymes which may benefit from modification in accordance with the present invention are characterised by a high sequence identity with SEQ ID NO. 1 (a particular region of the finger domain of the PB enzyme) and an aspartic acid residue at position 18 or the equivalent position in other enzymes/sequences. An "equivalent aspartic acid residue in other sequences" than SEQ ID NO. 1 (or other sequences) can be readily identified by using standard sequence alignment techniques such as Clustal X2 (Larkin, M. A. et al. (2007) Clustal W and Clustal X version 2.0. Bioinformatics, 23:2947-2948).

Of course, SEQ ID NO. 1 does not itself define a fully functional DNA polymerase. In preferred embodiments the DNA polymerase of the present invention is based on the amino acid sequence of PB DNA polymerase I, preferably which lacks the 5'-3'-exonuclease domain that is present in the wild-type *Psychrobacillus* species DNA polymerase I sequence. In preferred embodiments, the 5'-3'-exonuclease domain is absent from the DNA polymerase enzyme as 5'-3'-exonuclease activity is typically unwanted as it may degrade primers and/or products in an amplification mixture. This truncated wild-type PB sequence is referred to herein as SEQ ID NO. 2.

The invention provides a DNA polymerase comprising or consisting of the amino acid sequence of SEQ ID NO:2 or an amino acid sequence which is at least 60% identical to SEQ ID NO:2 but wherein the aspartic acid residue at position 422 of SEQ ID NO. 2, or the equivalent aspartic acid residue in other sequences, has been replaced by a non-negatively charged amino acid residue.

In preferred aspects and embodiments, the DNA polymerase of the invention comprises (or consists of) an amino acid sequence that is at least 70%, or 75%, preferably at least 80%, 85%, 90% or 95%, e.g. at least 98% or 99% or 99.5%, identical to SEQ ID NO:2 but wherein the aspartic acid residue at position 422 of SEQ ID NO. 2, or the equivalent aspartic acid residue in other sequences, has been replaced by a non-negatively charged amino acid residue. It will be understood that position 18 in SEQ ID NO. 1 and 422 in SEQ ID NO. 2 are equivalent, SEQ ID NO. 1 is a fragment from position 405 to 436 of SEQ ID NO. 2.

FIG. 5 shows an alignment of PB, Bst and Ubts DNA polymerases. The key Asp residue is at position 422 in each case.

In further preferred embodiments or aspects, the DNA polymerase of the invention comprises (or consists of) an amino acid sequence that is at least 60%, 70% or 75%, preferably at least 80%, 85%, 90% or 95%, e.g. at least 98% or 99% or 99.5%, identical to SEQ ID NO. 11 or 12 but wherein the aspartic acid residue at position 422 of SEQ ID NO. 11 or 12, or the equivalent aspartic acid residue in other sequences, has been replaced by a non-negatively charged amino acid residue. Numbering is based on a sequence alignment according to FIG. 5. SEQ ID NOs. 11 and 12 are the (truncated) variants of the wild type Bst and Ubts polymerase sequences respectively.

Preferably, the DNA polymerase of the invention comprises or consists of the amino acid sequence of SEQ ID NO:2, 11 or 12 but wherein the aspartic acid residue at position 422 of SEQ ID NO. 2, 11 or 12, or the equivalent aspartic acid residue in other sequences, has been replaced by a non-negatively charged amino acid residue.

In one embodiment, the DNA polymerase comprises (or consists of) the amino acid sequence of SEQ ID NO:4 (incorporating also the 5'→3' exonuclease domain) or a variant or fragment thereof but wherein the aspartic acid residue at position 719 of SEQ ID NO. 4, or the equivalent aspartic acid residue in other sequences, has been replaced by a non-negatively charged amino acid residue. The types of variants and fragments of SEQ ID NO:2 described herein apply, mutatis mutandis, to variants and fragments of SEQ ID NO:4, e.g. variants will have at least 70% preferably at least 80% or 90% sequence identity to SEQ ID.NO:4.

DNA polymerases of the invention include enzymatically active fragments of native polymerases. Enzymatically active fragments are fragments that have DNA polymerase activity. Enzymatically active fragments may be at least 400, at least 450, at least 475, at least 500, at least 525, at least 550, at least 560, at least 570 or at least 575 amino acids in length. Preferred fragments are at least 525, at least 550, at least 560, at least 570 or at least 575 amino acids in length. The fragments are at least 70%, preferably at least 80%, at least 85% or at least 90%, more preferably at least 95% (e.g. at least 98% or 99% or 99.5%), or 100% identical to the corresponding portion of SEQ ID NO:2, 11 or 12 but wherein the aspartic acid residue at position 422 of SEQ ID NO. 2, 11 or 12, or the equivalent aspartic acid residue in other sequences, has been replaced by a non-negatively charged amino acid residue.

DNA polymerase activity may be assessed using a molecular beacon that bears a loop structure and uses FAM as fluorescence donor and Dabcyl as an acceptor (non-fluorescent quencher) within an 8mer stem. This stem bears a 3'-extension that allows binding of a primer and acts as template for the DNA polymerase. The stem will be opened by the DNA polymerase when the extension proceeds. The following separation of the two labels is recorded by restoration of FAM emission. A suitable assay of this type is described in the Examples.

The DNA polymerases of the present invention have good strand displacement activity. This is an important property as in many isothermal amplification methods success relies on the inherent strand displacement activity of the DNA polymerase used in the reaction setup. The term "strand displacement" describes the ability of the polymerase to displace downstream DNA encountered during synthesis.

Suitable assays to assess strand displacement activity of a DNA polymerase are known in the art and a skilled person is readily able to select a suitable assay. In an exemplary strand displacement activity assay, a "cold" primer and a reporter strand that is labelled with a fluorophore (e.g. TAMRA) at its 3' end are annealed to a template strand that has a quencher (e.g. BHQ2) at its 5' end (the fluorophore is thus quenched by the close proximity of the quencher) such that there is a one nucleotide gap between the 3' end of the annealed "cold" primer and the 5' end of the annealed reporter strand; upon strand displacement activity of the DNA polymerase the fluorophore labelled oligonucleotide (reporter strand) is displaced from the template strand and as a consequence the fluorophore and quencher are no longer in close proximity and an increase in fluorescence can be measured.

Strand displacement activity may be assessed in an assay having the steps of (i) providing a template DNA molecule that has a quencher (fluorescence quencher) at its 5' end, (ii) annealing to said template DNA molecule a cold primer (i.e. non-fluorescent oligonucleotide) and a reporter strand (reporter oligonucleotide) that is labelled with a fluorophore at its 3' end wherein there is a one nucleotide gap between the 3' end of the annealed "cold" primer and the 5' end of the annealed reporter strand, whereby the quencher quenches the fluorophore by virtue of their close proximity to each other, (iii) incubating said template-cold primer-reporter strand complex with a DNA polymerase, $Me^{2+}$ and dNTPs and (iv) measuring the increasing fluorescence of the previously quenched fluorophore, wherein said fluorescence is indicative of strand displacement activity.

Preferred primers, reporter strands and template strands are as described in the Examples.

In a preferred embodiment strand displacement activity (SDA) is as assessed in accordance with the strand displacement activity assay described in the Example section. SDA is preferably measured at about the optimum temperature for that polymerase. For PB and other mesophiles that may be around 25° C.-37° C.

The present invention allows the SDA of a wild type DNA polymerase to be enhanced. In the case of PB the SDA is already high compared to most commercially available polymerases but SDA can still be significantly increased (see FIG. 3) by implementing the amino acid modification at position 18/422 described herein. For thermostable polymerases included in the invention, e.g. Ubts and Bst, the native SDA is quite low at ambient temperatures (25-37° C.). However the SDA is still significantly enhanced at 37° C. when the aspartic acid residue is replaced with a non-negatively charged amino acid residue. Different polymerases may be useful in different scenarios, e.g. Bst and Ubts are thermostable (Tm of 66° C. and 62° C. respectively), and so the ability to enhance SDA for any of these enzymes is very useful (see FIGS. 6 and 7).

Thus, in preferred embodiments, the DNA polymerases of the invention have at least 30%, preferably at least 50%, more preferably at least 100% greater SDA than a DNA polymerase with exactly the same sequence but with aspartic acid at position 18 or 422, relative to SEQ ID NOs. 1 and 2 respectively, or at the equivalent position in other sequences. Preferably the % increase observed will at least be seen under the conditions at which each enzyme exhibits its maximum SDA. In other words, for the best that each enzyme can perform, the polymerase of the invention will preferably have at least 30%, more preferably at least 50%, most preferably at least 100% higher SDA than its aspartic acid containing equivalent.

The aspartic acid residue discussed above, the modification of which is key to the benefits provided by the present invention, is replaced by a residue without a negative charge. The replacement will typically involve substitution with another amino acid residue but in some embodiments the aspartic acid residue may have been modified to remove its negative charge. Thus, the residue at position 18/422 of the polymerase of the invention will be either neutral or positively charged. Neutral amino acids include polar amino acids and hydrophobic amino acids. Suitable replacement amino acids include Ser, Thr, Asn, Gln, Ala, Ile, Leu, Tyr, Val, Lys and Arg. Non-standard, i.e. non-genetically coded amino acids, may be incorporated which are neutral or positively charged. Ala is particularly preferred.

The inventors have also found that some of the polymerases of the invention exhibit improved SDA performance at elevated [NaCl] and [KCl] as compared to enzymes which contain the Asp residue discussed above (see tables 2 and 4). Enhanced salt tolerance is thus a further benefit which may be provided by the present invention.

Preferred DNA polymerases of the present invention have useful levels of polymerase activity across a range of salt (NaCl and/or KCl) concentrations. Put another way, preferred DNA polymerases of the present invention exhibit across a broad range of salt concentrations a substantial proportion of the DNA polymerase activity observed at the salt concentration at which maximum polymerase activity is observed. Suitable assays for determining DNA polymerase activity are described elsewhere herein. A preferred assay for determining DNA polymerase activity is as described in the Example section.

In some embodiments, across a concentration range from about 20 mM to 200 mM NaCl or KCl or a mixture thereof, DNA polymerases of the present invention exhibit a substantial proportion (e.g. at least 40%, preferably at least 50%, more preferably at least 60%) of their maximum polymerase activity.

In a further aspect the present invention provides molecules (e.g. proteins, such as fusion proteins) comprising DNA polymerases of the present invention.

As used throughout the entire application, the terms "a" and "an" are used in the sense that they mean "at least one", "at least a first", "one or more" or "a plurality" of the referenced components or steps, except in instances wherein an upper limit or exclusion is thereafter specifically stated. The operable limits and parameters of combinations, as with the amounts of any single agent, will be known to those of ordinary skill in the art in light of the present disclosure.

Nucleic acid molecules comprising nucleotide sequences that encode DNA polymerases of the present invention as defined herein or fragments thereof, or nucleic acid molecules substantially homologous thereto, form yet further aspects of the invention. A preferred nucleic acid molecule is a nucleic acid encoding a DNA polymerase I of SEQ ID NO:2, or a sequence substantially homologous thereto (e.g. at least 60%, 70%, 75%, 80%, 85%, 90% or 95% identical thereto), but wherein the aspartic acid residue at position 422 of SEQ ID NO. 2, or the equivalent aspartic acid residue in other sequences, has been replaced by a non-negatively charged amino acid residue.

A preferred nucleic acid molecule comprises (or consists of) the nucleotide sequence as set forth in SEQ ID NO: 13, 14 or 15, or is a sequence substantially homologous thereto. Optionally, the final three nucleotides of SEQ ID NO: 13, 14 or 15 may be omitted. Nucleic acid sequences of the invention include sequences having at least 70% or 75%, preferably at least 80%, and even more preferably at least 85%, 90%, 95%, 96%, 97%, 98%, 99% or 99.5%, sequence identity to SEQ ID NO: 13, 14 or 15. Nucleic acid sequences of the invention thus include single or multiple base alterations (additions, substitutions, insertions or deletions) to the sequence of SEQ ID NO: 13, 14 or 15.

A particularly preferred nucleic acid molecule comprises or consists of the nucleotide sequence as set forth in SEQ ID NO: 13, 14 or 15.

The present invention also extends to nucleic acid molecules comprising (or consisting of) nucleotide sequences which are degenerate versions of nucleic acid molecules described herein, e.g. degenerate versions of a nucleic acid molecule comprising (or consisting of) SEQ ID NO: 13, 14 or 15.

Nucleic acid molecules of the invention are preferably "isolated" or "purified".

Homology (e.g. sequence identity) may be assessed by any convenient method. However, for determining the degree of homology (e.g. identity) between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA*, 89:10915-10919, 1992) and a gap opening penalty of 10 and gap extension penalty of 0.1, so that the highest order match is obtained between two sequences wherein at least 50% of the total length of one of the sequences is involved in the alignment. Clustal X is a convenient windows interface for Clustal W (Thompson, J. D. et al (1997) The ClustalX windows interface: flexible strategies for multiple sequence alignment aided by quality analysis tools. Nucleic Acids Research, 25:4876-4882).

Other methods that may be used to align sequences are the alignment method of Needleman and Wunsch (Needleman and Wunsch, *J. Mol. Biol.*, 48:443, 1970) as revised by Smith and Waterman (Smith and Waterman, *Adv. Appl. Math.*, 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS*, 4:11-17, 1988), FASTA (Pearson and Lipman, *Proc. Natl. Acad. Sci. USA*, 85:2444-2448, 1988; Pearson, *Methods in Enzymology*, 183:63-98, 1990) and gapped BLAST (Altschul et al., *Nucleic Acids Res.*, 25:3389-3402, 1997), BLASTP, BLASTN, or GCG (Devereux, Haeberli, Smithies, *Nucleic Acids Res.*, 12:387, 1984) are also useful for this purpose. Furthermore, the Dali server at the European Bioinformatics institute offers structure-based alignments of protein sequences (Holm, *Trends in Biochemical Sciences*, 20:478-480, 1995; Holm, *J. Mol. Biol.*, 233:123-38, 1993; Holm, *Nucleic Acid Res.*, 26:316-9, 1998).

By way of providing a reference point, sequences according to the present invention having 60%, 70%, 75%, 80%, 85%, 90%, 95%, 96%, 97%, 98% or 99%, sequence identity etc. may be determined using the ALIGN program with default parameters (for instance available on Internet at the GENESTREAM network server, IGH, Montpellier, France).

A "conservative amino acid substitution", as used herein, is one in which the amino acid residue is replaced with another amino acid residue having a similar side chain. Families of amino acid residues having similar side chains have been defined in the art.

DNA polymerases of the present invention comprise genetically encoded amino acids, but may also contain one or more non-genetically encoded amino acids.

When used in connection with a protein or polypeptide molecule such as a DNA polymerase, the term "isolated" or "purified" typically refers to a protein substantially free of cellular material or other proteins from the source from which it is derived. In some embodiments, such isolated or purified proteins are substantially free of culture medium when produced by recombinant techniques, or chemical precursors or other chemicals when chemically synthesized.

In one further aspect the present invention provides an expression vector (preferably a recombinant expression vector) containing a nucleic acid molecule of the invention, or a fragment thereof, and the necessary regulatory sequences for the transcription and translation of the protein sequence encoded by the nucleic acid molecule of the invention.

Possible expression vectors include but are not limited to cosmids or plasmids, so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

Suitable regulatory sequences may be derived from a variety of sources, including bacterial, fungal, viral, mammalian, or insect genes and are well known in the art. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention.

The recombinant expression vectors may also contain genes that encode a fusion moiety that provides increased expression of the recombinant protein; increased solubility of the recombinant protein and/or aids in the purification of the target recombinant protein by acting as a ligand in affinity purification (for example appropriate "tags" to enable purification and/or identification may be present, e.g., His tags or myc tags).

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. Suitable methods for transforming and transfecting host cells can be found in Sambrook et al., 1989 (Sambrook, Fritsch and Maniatis, *Molecular Cloning: A Laboratory Manual,* 2nd Ed., Cold Spring Harbor Press, Cold Spring Harbor, N.Y., 1989) and other laboratory textbooks.

Suitable host cells include a wide variety of prokaryotic host cells and eukaryotic cells. Preferably, proteins of the invention may be expressed in bacterial host cells, such as *Escherichia coli.*

N-terminal or C-terminal fusion proteins comprising DNA polymerases and proteins of the invention conjugated to other molecules, such as proteins (e.g. epitope tags), may be prepared by fusing through recombinant techniques.

A yet further aspect provides a host cell or virus comprising one or more expression constructs or expression vectors of the invention. Also provided are host cells or viruses comprising one or more of the nucleic acid molecules of the invention. A host cell or virus capable of expressing a DNA polymerase of the invention forms a yet further aspect. Preferred host cells include Rosetta 2 (DE3) cells (Novagen).

DNA polymerases of the invention may be produced recombinantly in a host cell and isolated and purified therefrom. The DNA polymerases of the invention may therefore be considered recombinant enzymes, in particular isolated recombinant enzymes. In certain embodiments the DNA polymerase is produced by recombinant techniques in a host cell that is not, or not from, an organism which is the same as that from which the DNA polymerase was derived.

DNA polymerases of the present invention may be generated using recombinant DNA technology. Alternatively, a cell-free expression system can be used for production of the DNA polymerase. Alternatively, DNA polymerases of the present invention may be generated using chemical synthesis so that the DNA polymerase is generated by stepwise elongation, one amino acid at a time. Such chemical synthesis techniques (e.g. solid phase synthesis) are well known in the chemistry of proteins.

A further aspect of the invention provides a method of producing a DNA polymerase of the present invention comprising a step of culturing the host cells of the invention. Preferred methods comprise the steps of (i) culturing a host cell comprising one or more of the recombinant expression vectors or one or more of the nucleic acid molecules of the invention under conditions suitable for the expression of the encoded DNA polymerase or protein; and optionally (ii) isolating or obtaining the DNA polymerase or protein from the host cell or from the growth medium/supernatant. Such methods of production may also comprise a step of purification of the DNA polymerase or protein product and/or formulating the DNA polymerase or product into a composition including at least one additional component, such as an acceptable buffer or carrier.

The DNA polymerase may be separated, or isolated, from the host cells/culture media using any of the purification techniques for protein known in the art and widely described in the literature or any combination thereof. Such techniques may include for example, precipitation, ultrafiltration, dialysis, various chromatographic techniques, e.g. size exclusion chromatography, ion-exchange chromatography, affinity chromatography, electrophoresis, centrifugation etc. As discussed above, the DNA polymerase of the invention may be modified to carry amino acid motifs or other protein or non-protein tags, e.g. polyhistidine tags (e.g. $His_6$-tag), to assist in isolation, solubilisation and/or purification or identification.

In another aspect, the present invention provides the use of a DNA polymerase of the invention for nucleotide (e.g. dNTP) polymerisation. Accordingly, DNA polymerases of the invention may be used to extend a nucleic acid (DNA) strand by one or more nucleotides.

In another aspect, the present invention provides the use of a DNA polymerase of the invention in a nucleic acid (DNA) amplification or sequencing reaction.

In another aspect, the present invention provides the use of a DNA polymerase of the invention in a molecular beacon assay or in a strand displacement assay, e.g. as described herein.

Preferably, in uses and methods of the present invention, DNA polymerases of the present invention are used at a constant temperature, i.e. without thermal cycling. Accordingly, the use of DNA polymerases of the invention in isothermal reactions is particularly preferred.

The use of DNA polymerases of the invention in isothermal amplification reactions is particularly preferred. Isothermal reactions are performed at a constant temperature. Many isothermal amplification techniques are known in the art and include Loop mediated isothermal amplification (LAMP), rolling circle amplification (RCA), strand displacement amplification (SDA), multiple displacement amplification (MDA) and cross priming amplification (CPA).

In another aspect, the present invention provides a method of nucleotide polymerisation using a DNA polymerase of the present invention. Preferably, said method comprises providing a reaction mixture comprising a DNA polymerase of the present invention, a template nucleic acid molecule, an oligonucleotide primer which is capable of annealing to a portion of the template nucleic acid molecule and one or more species of nucleotide (e.g. deoxynucleoside triphosphates, dNTPs) and incubating said reaction mixture under conditions whereby the oligonucleotide primer anneals to the template nucleic acid molecule and said DNA polymerase extends said oligonucleotide primer by polymerising one or more nucleotides. Suitable conditions are well known in the art. Preferably a constant temperature is used and preferred temperatures are set out elsewhere herein. Optionally, the generation of the polynucleotide product is detected (e.g. via gel electrophoresis).

In another aspect, the present invention provides a method of amplifying a nucleic acid (DNA) using a DNA polymerase of the present invention. Typically, said method comprises providing a reaction mixture comprising a DNA polymerase of the present invention, a template nucleic acid molecule, an oligonucleotide primer(s) (e.g. 2 or more primers such as 2, 3, 4, 5 or 6 primers) which is capable of annealing to a portion of the template nucleic acid molecule acid molecule, and nucleotides (e.g. deoxynucleoside triphosphates, dNTPs) and incubating said reaction mixture under conditions whereby the oligonucleotide primer(s) anneals to the template nucleic acid molecule and said DNA polymerase extends said oligonucleotide primer(s) by polymerising one or more nucleotides to generate a polynucleotide. Suitable conditions are well known in the art. Preferred methods of nucleic acid amplification are isothermal amplification methods. Isothermal amplification methods of the invention are performed at a constant temperature and preferred temperatures are set out elsewhere herein. Optionally, the generation of the polynucleotide product is detected (e.g. via gel electrophoresis).

Exemplary isothermal amplification methods include Loop mediated isothermal amplification (LAMP), rolling circle amplification (RCA), strand displacement amplification (SDA), multiple displacement amplification (MDA) and cross priming amplification (CPA).

In some embodiments, particularly those using DNA polymerases based on the PB sequence, the constant temperature used in the methods and uses of the present invention is a low-to-moderate temperature, for example, is chosen from within the range 0° C. to about 42° C., preferably is chosen from within the range about 10° C. to about 40° C., or about 20° C. to about 40° C., or about 25° C. to about 40° C., or about 30° C. to about 40° C. or about 35° C. to about 40° C., or about 37° C. to about 40° C. In some embodiments, the constant temperature is chosen from within the range about 10° C. to about 15° C., or about 10° C. to about 20° C. In some embodiments, the constant temperature is chosen from within the range about 10° C. to about 30° C. In some embodiments, the constant temperature is chosen from within the range about 20° C. to about 30° C. In some embodiments, the constant temperature is chosen from within the range about 10° C. to about 25° C. In some embodiments, the constant temperature is chosen from within the range about 20° C. to about 25° C. A constant temperature of about 25° C. is preferred. In some embodiments, the constant temperature is 25° C.

With other polymerases of the invention, for example those based on sequences from organisms which are thermophilic, the constant temperature may be moderate to high, e.g. is chosen from within the range 25° C.-65° C., preferably 40° C.-65° C.

A temperature may be considered constant when no active steps are taken to modify the temperature during the reaction, e.g. no thermal cycling. A 'constant' temperature may still allow temperature fluctuations during the method e.g. of up to about 5° C., typically no more than 3° C. or 2° C.

DNA polymerases of the present invention may be used in point-of-care molecular diagnostics platforms.

DNA polymerases of the present invention may be used in whole genome amplification.

DNA polymerases of the present invention may be used in next-generation sequencing methods. So-called "next generation" or "second generation" sequencing approaches (in reference to the Sanger dideoxynucleotide method as the "first generation" approach) have become widespread. These newer techniques are characterised by high throughputs, e.g. as a consequence of the use of parallel, e.g. massively parallel sequencing reactions, or through less time-consuming steps. Various high throughput sequencing methods provide single molecule sequencing and employ techniques such as pyrosequencing, reversible terminator sequencing, cleavable probe sequencing by ligation, non-cleavable probe sequencing by ligation, DNA nanoballs, and real-time single molecule sequencing.

References herein to DNA polymerases of the invention encompass active fragments unless otherwise clear from the context.

Uses and methods of the present invention are typically performed in vitro.

The present invention also provides compositions comprising a DNA polymerase of the invention. Such compositions preferably comprise a buffer. Optionally, compositions of the present invention further comprise one or more of the necessary reagents to carry out a nucleic acid amplification reaction (e.g. an isothermal amplification reaction), e.g. oligonucleotide primers capable of annealing to a region of the template DNA to be amplified and/or nucleotides (e.g. dNTPs). Typically compositions will be aqueous and buffered with a standard buffer such as Tris, HEPES, etc.

The invention further includes kits comprising one or more of the DNA polymerases of the invention, or one or more compositions of the invention, or one or more of the nucleic acid molecules of the invention, or one or more expression vectors of the invention, or one or more host cells or viruses of the invention. Preferably said kits are for use in the methods and uses as described herein, e.g., in nucleic acid amplification methods, such as isothermal amplification reactions. Preferably said kits comprise instructions for use of the kit components, for example for nucleic acid amplification.

Nucleotide and Amino Acid Sequences Disclosed Herein and their Sequence Identifiers (Seq Id Nos)

All nucleotide sequences are recited herein 5' to 3' in line with convention in this technical field.

SEQ ID NO: 1-amino acid sequence of a region of the finger domain of DNA
polymerase I from a *Psychrobacillus* sp.
SEQ ID NO: 1
MRRAAKAVNFGIVYGISDYGLSQNLDITRKEA SEQ ID NO: 2-amino acid sequence of truncated DNA polymerase I isolated from
a *Psychrobacillus* sp. (PB)
SEQ ID NO: 2
TEVAFEIVEEIDSTILDKVMSVHLEMYDGQYHTSELLGIALSDGEKGYFAPADIAFQ
SKDFCSWLENATNKKYLADSKATQAVSRKHNVNVHGVEFDLLLAAYIVNPAISSED
VAAIAKEFGYFNLLTNDSVYGKGAKKTAPEIEKIAEHAVRKARAIWDLKEKLEVKLE

```
ENEQYALYKEIELPLASILGTMESDGVLVDKQILVEMGHELNIKLRAIEQDIYALAGE
TFNINSPKQLGVILFEKIGLTPIKKTKTGYSTAADVLEKLASEHEIIEQILLYRQLGKLN
STYIEGLLKEIHEDDGKIHTRYQQALTSTGRLSSINPNLQNIPVRLEEGRKIRKAFVP
SQPGWVMFAADYSQIELRVLAHMSEDENLVEAFNNDLDIHTKTAMDVFHVEQEAV
TSDMRRAAKAVNFGIVYGISDYGLSQNLDITRKEAATFIENYLNSFPGVKGYMDDIV
QDAKQTGYVTTILNRRRYLPEITSSNFNLRSFAERTAMNTPIQGSAADIIKKAMIDM
AERLISENMQTKMLLQVHDELIFEAPPEEIAMLEKIVPEVMENAIKLIVPLKVDYAFG
SSWYDTK

SEQ ID NO: 3-nucleic acid sequence encoding the *Psychrobacillus* species DNA
polymerase I sequence of SEQ ID NO: 2
SEQ ID NO: 3
ACAGAAGTAGCATTCGAGATTGTTGAAGAAATTGACTCTACAATATTAGATAAA
GTAATGTCAGTCCATTTAGAAATGTATGATGGGCAATATCATACAAGCGAATTA
TTAGGTATTGCTTTATCAGATGGAGAAAAGGGTTATTTTGCTCCTGCTGATATA
GCTTTTCAATCGAAGGATTTTTGTTCTTGGTTAGAAAATGCTACGAATAAAAAG
TATTTAGCAGACTCCAAAGCAACACAAGCAGTGAGTAGAAAACATAATGTGAAT
GTACATGGAGTGGAATTCGACCTTCTTTTAGCAGCGTATATAGTAAATCCTGCT
ATCTCTTCAGAGGATGTTGCTGCTATTGCTAAAGAATTTGGATATTTTAACTTG
CTGACAAACGATAGTGTTTATGGGAAAGGTGCCAAAAAAACCGCACCTGAAAT
CGAGAAAATTGCAGAACATGCCGTAAGAAAAGCAAGGGCTATTTGGGACTTGA
AAGAAAAGTTAGAAGTAAAACTGGAAGAAAATGAACAATATGCGTTGTATAAAG
AAATAGAGCTACCGCTTGCATCTATCCTTGGTACGATGGAATCAGATGGGGTG
CTGGTGGATAAACAAATTCTTGTAGAAATGGGTCATGAGCTTAATATTAAGTTA
CGAGCGATTGAACAAGACATTTATGCGTTAGCTGGTGAAACGTTTAATATTAAT
TCACCTAAACAATTAGGTGTAATACTATTTGAAAAAATTGGTCTTACCCCTATTA
AAAAGACAAAAACGGGCTATTCAACTGCAGCAGATGTTTTGGAAAAACTAGCA
AGTGAACATGAAATAATAGAGCAAATTTTACTATATCGTCAATTAGGTAAACTCA
ATTCCACATATATCGAAGGATTATTAAAAGAGATTCATGAAGATGATGGGAAGA
TCCATACCCGATATCAACAAGCCCTAACTTCAACTGGGCGTTTGAGTTCGATC
AATCCAAACCTTCAAAATATACCAGTTCGTTTAGAAGAAGGTAGAAAAATACGT
AAAGCCTTTGTTCCTTCACAACCGGGATGGGTAATGTTTGCGGCGGATTACTC
TCAAATTGAATTGCGTGTTCTTGCCCATATGTCTGAGGATGAAAACCTGGTAGA
AGCTTTTAATAATGATCTGGATATTCATACTAAAACGGCTATGGATGTATTCCAT
GTGGAGCAGGAAGCAGTAACGTCCGATATGCGCCGTGCTGCTAAGGCAGTTA
ACTTTGGGATTGTGTATGGTATTAGTGATTATGGTTTATCACAAAACCTAGATAT
TACTAGAAAAGAAGCGGCGACATTTATCGAGAATTATTTAAATAGCTTCCCAGG
TGTAAAAGGATATATGGATGATATCGTTCAAGATGCGAAACAAACAGGCTACG
TTACAACAATTTTGAATAGACGAAGATATTTGCCTGAAATAACAAGTTCTAACTT
TAATCTCCGCAGTTTTGCAGAACGTACTGCTATGAATACACCAATTCAAGGGA
GTGCAGCCGATATTATTAAAAAAGCAATGATCGATATGGCGGAAAGATTAATAT
CAGAAAATATGCAGACCAAAATGCTACTACAAGTACATGATGAATTAATTTTTG
AGGCTCCACCAGAGGAAATTGCAATGCTAGAAAAAATAGTGCCAGAGGTGATG
GAAAACGCTATTAAACTGATTGTACCTTTGAAAGTGGATTATGCCTTTGGTTCA
TCTTGGTATGACACGAAGTAG SEQ ID NO: 4-amino acid sequence of full-length DNA polymerase I isolated from
a *Psychrobacillus* sp.
SEQ ID NO: 4
MYLSTEKILLLDGNSLAYRAFFALPLLTNEHGIHTNAVYGFTMMLQKIMDEENPTHMLVA
FDAGKTTFRHSTFGDYKGGRQKTPPELSEQFPYIRKLIDAYGIKRYELEMYEADDIIGTL
SKRADEKGQQVVIVSGDKDLTQLATDKTTVYITRKGITDIEKYTPEHVQEKYGLTPLQII
DMKGLMGDASDNIPGVPGVGEKTAIKLLKEHGSVEDLYKALDTVSGVKLKEKLIANEEQA
IMSKALATIETAAPIQISIDDLSYTGPNMEEVIEVWKELAFKTLLEKSDYISEESETTEV
AFEIVEEIDSTILDKVMSVHLEMYDGQYHTSELLGIALSDGEKGYFAPADIAFQSKDFCS
WLENATNKKYLADSKATQAVSRKHNVNVHGVEFDLLLAAYIVNPAISSEDVAAIAKEFGY
FNLLTNDSVYGKGAKKTAPEIEKIAEHAVRKARAIWDLKEKLEVKLEENEQYALYKEIEL
PLASILGTMESDGVLVDKQILVEMGHELNIKLRAIEQDIYALAGETFNINSPKQLGVILF
EKIGLTPIKKTKTGYSTAADVLEKLASEHEIIEQILLYRQLGKLNSTYIEGLLKEIHEDD
GKIHTRYQQALTSTGRLSSINPNLQNIPVRLEEGRKIRKAFVPSQPGWVMFAADYSQIEL
RVLAHMSEDENLVEAFNNDLDIHTKTAMDVFHVEQEAVTSDMRRAAKAVNFGIVYGISDY
GLSQNLDITRKEAATFIENYLNSFPGVKGYMDDIVQDAKQTGYVTTILNRRRYLPEITSS
NFNLRSFAERTAMNTPIQGSAADIIKKAMIDMAERLISENMQTKMLLQVHDELIFEAPPE
EIAMLEKIVPEVMENAIKLIVPLKVDYAFGSSWYDTK SEQ ID NO: 5-nucleic acid sequence encoding the *Psychrobacillus* sp. DNA
polymerase I sequence of SEQ ID NO: 4.
SEQ ID NO: 5
ATGTATTTGTCAACCGAGAAAATCCTATTATTAGACGGCAATAGTTTGGCATAC
CGAGCTTTTTTTGCCCTACCTTTATTAACAAATGAACATGGAATACATACAAAC
GCAGTATATGGCTTTACAATGATGCTACAAAAAATTATGGATGAAGAAAATCCT
ACTCATATGCTCGTGGCATTTGATGCCGGGAAAACGACCTTCCGTCACTCTAC
TTTTGGGGATTATAAAGGTGGAAGACAAAAAACACCACCAGAACTATCGGAAC
AATTCCCTTATATACGCAAGTTAATCGATGCTTATGGTATTAAGCGATACGAAC
TGGAAATGTACGAAGCAGACGATATTATCGGTACTTTAAGCAAGCGTGCAGAC
GAAAAAGGGCAGCAAGTTGTAATTGTCTCAGGTGATAAAGATTTAACACAACTA
GCTACAGATAAAACAACTGTGTATATCACAAGAAAAGGCATAACCGATATTGAA
AAATATACACCTGAACATGTACAAGAAAAGTATGGCTTAACTCCATTACAGATT
ATAGACATGAAAGGTTTAATGGGAGATGCTTCTGATAATATTCCAGGAGTTCCT
```

-continued

```
GGTGTCGGAGAAAAAACAGCTATTAAGCTTTTAAAAGAACATGGTTCGGTAGA
GGATTTATATAAAGCACTTGATACAGTTAGTGGTGTTAAACTAAAGGAAAAACT
CATCGCCAACGAAGAGCAGGCAATTATGAGTAAGGCATTAGCTACGATTGAAA
CAGCTGCACCGATACAGATTTCTATAGACGATCTTTCATATACTGGTCCTAATA
TGGAAGAAGTAATTGAAGTTTGGAAGGAACTAGCTTTTAAAACTCTTCTTGAGA
AATCTGACTATATTTCTGAGGAATCCGAAACTACAGAAGTAGCATTCGAGATTG
TTGAAGAAATTGACTCTACAATATTAGATAAAGTAATGTCAGTCCATTTAGAAAT
GTATGATGGGCAATATCATACAAGCGAATTATTAGGTATTGCTTTATCAGATGG
AGAAAAGGGTTATTTTGCTCCTGCTGATATAGCTTTTCAATGAAGGATTTTTG
TTCTTGGTTAGAAAATGCTACGAATAAAAAGTATTTAGCAGACTCCAAAGCAAC
ACAAGCAGTGAGTAGAAAACATAATGTGAATGTACATGGAGTGGAATTCGACC
TTCTTTTAGCAGCGTATATAGTAAATCCTGCTATCTCTTCAGAGGATGTTGCTG
CTATTGCTAAAGAATTTGGATATTTTAACTTGCTGACAAACGATAGTGTTTATGG
GAAAGGTGCCAAAAAAACCGCACCTGAAATCGAGAAAATTGCAGAACATGCCG
TAAGAAAAGCAAGGGCTATTTGGGACTTGAAAGAAAAGTTAGAAGTAAAACTG
GAAGAAAATGAACAATATGCGTTGTATAAAGAAATAGAGCTACCGCTTGCATCT
ATCCTTGGTACGATGGAATCAGATGGGGTGCTGGTGGATAAACAAATTCTTGT
AGAAATGGGTCATGAGCTTAATATTAAGTTACGAGCGATTGAACAAGACATTTA
TGCGTTAGCTGGTGAAACGTTTAATATTAATTCACCTAAACAATTAGGTGTAAT
ACTATTTGAAAAATTGGTCTTACCCCTATTAAAAAGACAAAACGGGCTATTC
AACTGCAGCAGATGTTTTGGAAAAACTAGCAAGTGAACATGAAATAATAGAGC
AAATTTTACTATATCGTCAATTAGGTAAACTCAATTCCACATATATCGAAGGATT
ATTAAAAGAGATTCATGAAGATGATGGGAAGATCCATACCCGATATCAACAAG
CCCTAACTTCAACTGGGCGTTTGAGTTCGATCAATCCAAACCTTCAAATATAC
CAGTTCGTTTAGAAGAAGGTAGAAAAATACGTAAAGCCTTTGTTCCTTCACAAC
CGGGATGGGTAATGTTTGCGGCGGATTACTCTCAAATTGAATTGCGTGTTCTT
GCCCATATGTCTGAGGATGAAAACCTGGTAGAAGCTTTTAATAATGATCTGGAT
ATTCATACTAAAACGGCTATGGATGTATTCCATGTGGAGCAGGAAGCAGTAAC
GTCCGATATGCGCCGTGCTGCTAAGGCAGTTAACTTTGGGATTGTGTATGGTA
TTAGTGATTATGGTTTATCACAAAACCTAGATATTACTAGAAAAGAAGCGGCGA
CATTTATCGAGAATTATTTAAATAGCTTCCCAGGTGTAAAAGGATATATGGATG
ATATCGTTCAAGATGCGAAACAAACAGGCTACGTTACAACAATTTTGAATAGAC
GAAGATATTTGCCTGAAATAACAAGTTCTAACTTTAATCTCCGCAGTTTTGCAG
AACGTACTGCTATGAATACACCAATTCAAGGGAGTGCAGCCGATATTATTAAAA
AAGCAATGATCGATATGGCGGAAAGATTAATATCAGAAAATATGCAGACCAAAA
TGCTACTACAAGTACATGATGAATTAATTTTTGAGGCTCCACCAGAGGAAATTG
CAATGCTAGAAAAAATAGTGCCAGAGGTGATGGAAAACGCTATTAAACTGATT
GTACCTTTGAAAGTGGATTATGCCTTTGGTTCATCTTGGTATGACACGAAGTAG
```

SEQ ID NOS: 6-10 are, like SEQ ID NO: 1, an amino acid sequence of a region of the finger domain of DNA polymerase I from *Bacillus* species C3_41*, *Ureibacillus thermosphaericus*, *Bacillus subtilis*, *Bacillus smithii* and *Geobacillus stearothermophilus* respectively (* = Bei etal. 2005, Arch Microbiol, 186: 203-209; Genbank accession number DQ309765).

SEQ ID NO: 6
MRRAAKAVNFGIVYGISDYGLSQNLDITRKEA

SEQ ID NO: 7
MRRAAKAVNFGHYGISDYGLSQNLDISRKEA

SEQ ID NO: 8
MRRQAKAVNFGIVYGISDYGLSQNLGITRKEA

SEQ ID NO: 9
MRRQAKAVNFGIVYGISDYGLSQNLGITRKEA

SEQ ID NO: 10
MRRQAKAVNFGIVYGISDYGLAQNLNISRKEA

SEQ ID NO: 11 is the amino acid sequence of truncated DNA polymerase I isolated from *Geobacillus stearothermophilus* (Bst).
SEQ ID NO: 11
AKMAFTLADRVTEEMLADKAALVVEVVEENYHDAPIVGIAVVNEHGRFFLRPETALADPQ
FVAWLGDETKKKSMFDSKRAAVALKWKGIELCGVSFDLLLAAYLLDPAQGVDDVAAAAKM
KQYEAVRPDEAVYGKGAKRAVPDEPVLAEHLVRKAAAIWELERPFLDELRRNEQDRLLVE
LEQPLSSILAEMEFAGVKVDTKRLEQMGKELAEQLGTVEQRIYELAGQEFNINSPKQLGV
ILFEKLQLPVLKKTKTGYSTSADVLEKLAPYHEIVENILHYRQLGKLQSTYIEGLLKVVR
PDTKKVHTIFNQALTQTGRLSSTEPNLQNIPIRLEEGRKIRQAFVPSESDWLIFAADYSQ
IELRVLAHIAEDDNLMEAFRRDLDIHTKTAMDIFQVSEDEVTPNMRRQAKAVNFGIVYGI
SDYGLAQNLNISRKEAAEFIERYFESPPGVKRYMENIVQEAKQKGYVTTLLHRRRYLPDI
TSRNFNVRSFAERMAMNTPIQGSAADIIKKAMIDLNARLKEERLQAHLLLQVHDELILEA
PKEEMERLCRLVPEVMEQAVTLRVPLKVDYHYGSTWYDAK SEQ ID NO: 12 is the amino acid sequence of truncated DNA polymerase I isolated from *Ureibacillus thermosphaericus* (Ubts)
SEQ ID NO: 12
AALSFKIVREIAEDLFTDTMAVHVELENEHYHTCNILGFGFTDGSNTFFVPTEVLQKSER
LKSYFEDETKKKYMSDLKAAQCILKRHGINLRGVEFDLLLASYIVNPAISGDDVATLAKE
FGYTDVRSNEAVYGKGAKWALPSEEVLAEHVCRKAFAIWSCKERVSNKLKENEQFDLYHD LELPLAVILGKMESEGIKVNISTLETMGQELEDKIAKLETEIYELAGETFNINSPKQLGV
ILFEKLGLPVIKKTKTGYSTAADVLEKLKSEHQIVQLILEYRTLAKLQSTYIEGLIKEVH
PKDSKVHTRFMQALTSTGRLSSTDPNLQNIPIRLEEGRKIRKAFVPSHDGWLLFSADYSQ
IELRVLAHMSKDKNLVEAFNQGMDIHTRTAMEVFHVSQDDVTSNMRRAAKAVNFGIIYGI
SDYGLSQNLDISRKEAGEFIEKYFESFPGVKEYMDNIVQEAKLKGYVTTILNRRRYLPDI
TSKNFNLRSFAERTAMNTPIQGSAADIIKKAMLDIDARLNSEGLQAKLLLQVHDELIFEA
PKEE1EKLEKIVPEVMESAILLDVPLKVDISYGETWYDAK SEQ ID NO: 13 is the codon optimised (for E.coli expression) nucleic acid sequence
encoding the PB D422A mutant.
SEQ ID NO: 13
ACCGAAGTTGCATTTGAAATTGTGGAAGAAATCGATAGCACCATCCTGGATAAAGTTAT
GAGCGTTCATCTGGAAATGTATGATGGTCAGTATCATACCAGCGAACTGCTGGGTATT
GCACTGAGTGATGGTGAAAAAGGTTATTTTGCACCGGCAGATATTGCCTTTCAGAGCAA
AGATTTTTGTAGCTGGCTGGAAATGCCACCAACAAAAAATACCTGGCAGATAGCAAAG
CAACCCAGGCAGTTAGCCGTAAACATAATGTTAATGTTCACGGCGTGGAATTTGATCTG
CTGCTGGCAGCATATATTGTTAATCCGGCAATTAGCAGCGAAGATGTTGCAGCAATTGC
AAAAGAATTCGGCTATTTTAACCTGCTGACCAACGATAGCGTTTATGGTAAAGGTGCAA
AAAAAACCGCACCGGAAATTGAAAAAATTGCCGAACATGCAGTTCGTAAAGCACGTGC
AATTTGGGATCTGAAAGAAAAACTGGAAGTGAAACTGGAAGAGAACGAACAGTATGCC
CTGTATAAAGAAATTGAACTGCCGCTGGCAAGCATTCTGGGCACCATGGAAAGTGATG
GTGTTCTGGTTGATAAACAAATCCTGGTTGAAATGGGTCACGAGCTGAACATTAAACTG
CGTGCAATTGAACAGGATATTTATGCACTGGCAGGCGAAACCTTTAACATTAATAGCCC
GAAACAGCTGGGTGTGATCCTGTTTGAAAAAATCGGTCTGACCCCGATCAAAAAAACC
AAAACCGGTTATAGCACCGCAGCAGATGTTCTGGAAAAACTGGCAAGCGAACATGAAA
TTATTGAGCAGATTCTGCTGTATCGTCAGCTGGGTAAACTGAATAGCACCTATATTGAA
GGTCTGCTGAAAGAAATCCATGAGGATGATGGTAAAATCCATACCCGTTATCAGCAGGC
ACTGACCAGCACCGGTCGTCTGAGCAGCATTAATCCGAATCTGCAGAATATTCCGGTTC
GTCTGGAAGAAGGTCGTAAAATTCGTAAAGCATTTGTTCCGAGCCAGCCTGGTTGGGT
TATGTTTGCAGCAGATTATAGCCAGATTGAACTGCGTGTTCTGGCACATATGAGCGAAG
ATGAAAATCTGGTTGAAGCCTTTAACAACGATCTGGATATTCATACCAAAACCGCCATG
GATGTTTTTCACGTTGAACAAGAAGCAGTTACCAGCGATATGCGTCGTCAGCAAAAG
CAGTTAATTTTGGTATTGTGTATGGCATCAGCGCTTATGGTCTGAGCCAGAATCTGGAT
ATTACCCGTAAAGAAGCAGCCACCTTTATCGAAAACTACCTGAATAGCTTTCCGGGTGT
GAAAGGCTATATGGATGATATTGTTCAGGATGCAAAACAGACCGGTTATGTTACCACCA
TTCTGAATCGTCGTCGTTATCTGCCGGAAATTACCAGCAGCAACTTTAATCTGCGTAGC
TTTGCAGAACGTACCGCAATGAATACCCCGATTCAGGGTAGCGCAGCAGATATTATCAA
AAAAGCCATGATTGATATGGCCGAACGTCTGATTAGCGAAAATATGCAGACCAAAATGC
TGCTGCAGGTTCATGATGAACTGATTTTTGAAGCACCGCCTGAAGAAATTGCAATGCTG
GAAAAAATTGTTCCGGAAGTGATGGAAAACGCCATTAAACTGATTGTTCCGCTGAAAGT
GGATTATGCATTTGGTAGCAGTTGGTACGATACCCAAATAA SEQ ID NO: 14-is the codon optimised nucleic acid sequence encoding the Bst
D→A mutant.
SEQ ID NO: 14
GCCAAAATGGCATTTACCCTGGCAGATCGTGTTACCGAAGAAATGCTGGCAGATAAAG
CAGCACTGGTTGTTGAAGTTGTGGAAGAAAATTATCATGATGCACCGATTGTTGGTATT
GCCGTTGTTAATGAACATGGCCGTTTTTTTCTGCGTCCGGAAACCGCACTGGCCGATC
CGCAGTTTGTTGCATGGCTGGGTGATGAAACCAAAAAAAAGAGCATGTTTGATAGCAA
CGTGCAGCAGTTGCACTGAAATGGAAAGGTATTGAACTGTGCGGTGTTTCATTTGATCT
GCTGCTGGCAGCATATCTGCTGGATCCGGCACAGGGTGTTGATGATGTTGCAGCAGC
AGCAAAGATGAAACAGTATGAAGCAGTTCGTCCGGATGAAGCCGTTTATGGTAAAGGT
GCAAAACGTGCCGTGCCGGATGAACCGGTGCTGGCCGAACATCTGGTTCGTAAAGCA
GCCGCAAATTTGGGAATTAGAACGTCCGTTTCTGGATGAACTGCGTCGTAATGAACAGG
ATCGTCTGCTGGTTGAACTGGAACAGCCGCTGAGCAGCATTCTGGCAGAAATGGAATT
TGCCGGTGTTAAAGTGGATACCAAACGTCTGGAACAAATGGGTAAAGAACTGGCAGAA
CAGCTGGGCACCGTTGAACAGCGTATTTATGAGCTGGCAGGTCAAGAATTTAACATCA
ATAGCCCGAAACAACTGGGCGTGATTCTGTTTGAAAAACTGCAGCTGCCGGTTCTGAA
AAAAACCAAAACCGGTTATAGCACCAGCGCAGATGTTCTGGAAAAACTGGCACCGTAT
CATGAAATTGTGGAAAACATTCTGCATTATCGCCAGCTGGGTAAACTGCAGAGCACCTA
TATTGAAGGTCTGCTGAAAGTTGTTCGTCCCGATACCAAAAAAGTGCACACCATTTTTA
ACCAGGCACTGACCCAGACCGGTCGTCTGAGCAGTACCGAACCGAATCTGCAGAATAT
TCCGATTCGTCTGGAAGAAGGTCGTAAAATTCGTCAGGCCTTTGTTCCGAGCGGAAGC
GATTGGCTGATTTTTGCAGCAGATTATAGCCAGATTGAACTGCGCGTTCTGGCACATAT
TGCCGAAGATGATAATCTGATGGAAGCATTTCGTCGCGATCTGGATATTCATACCAAAA
CAGCCATGGATATTTTTCAGGTGAGCGAAGATGAAGTTACCCCGAATATGCGTCGTCA
GGCAAAAGCAGTTAATTTTGGTATTGTGTATGGCATTAGCGCATATGGTCTGGCACAGA
ATCTGAATATTAGCCGTAAAGAAGCAGCCGAGTTTATCGAACGTTATTTGAAAGTTTTC
CGGGTGTGAAACGCTATATGGAAAATATTGTTCAAGAAGCCAAACAGAAAGGCTATGTT
ACCACACTGCTGCATCGTCGTCGTTATCTGCCGGATATTACCAGCCGTAACTTTAATGT
TCGTAGCTTTGCAGAACGTATGGCAATGAATACCCCGATTCAGGGTAGCGCAGCCGAT
ATTATCAAAAAAGCAATGATTGATCTGAACGCACGCCTGAAAGAAGAACGTCTGCAGG
CACATCTGCTGTTACAGGTTCATGATGAACTGATTCTGGAAGCCCCTAAAGAAGAGATG
GAACGTCTTTGTCGTCTGGTTCCGGAAGTTATGGAACAGGCAGTTACCCTGCGTGTTC
CGCTGAAAGTGGATTATCATTATGGTAGCACCTGGTATGATGCCAAATAA SEQ ID NO: 15-is the codon optimised nucleic acid sequence encoding the Ubts
D→A mutant.
SEQ ID NO: 15
GCAGCACTGAGCTTTAAAATCGTTCGTGAAATTGCAGAGGACCTGTTTACCGATACCAT
GGCAGTTCATGTTGAACTGGAAAACGAACATTATCACACGTGCAACATTCTTGGTTTTG
GTTTTACCGATGGCAGCAACACCTTTTTTGTTCCGACCGAAGTGCTGCAGAAAAGCGA
ACGTCTGAAAAGCTATTTTGAGGATGAAACCAAAAAAAAGTATATGAGCGATCTGAAAG
CAGCCCAGTGTATTCTGAAACGTCATGGTATTAATCTGCGTGGCGTTGAATTTGATCTG
CTGCTGGCAAGCTATATTGTTAATCCGGCAATTAGCGGTGATGATGTTGCAACCCTGG
CAAAAGAATTTGGCTATACCGATGTTCGTAGCAATGAAGCCGTTTATGGTAAAGGTGCA
AAATGGGCACTGCCGAGCGAAGAGGTTCTGGCAGAACATGTTTGTCGTAAAGCATTTG
CAATTTGGAGCTGCAAAGAACGCGTTAGCAATAAACTGAAAGAGAACGAACAGTTCGA
TCTGTATCATGATCTGGAACTGCCGCTGGCCGTTATTCTGGGTAAAATGGAAAGCGAA
GGCATCAAAGTGAATATCAGCACCCTGGAAACCATGGGTCAAGAACTGGAAGATAAAA
TTGCCAAACTGGAAACCGAGATCTATGAACTGGCAGGCGAAACCTTTAACATTAATAGC
CCGAAACAGCTGGGTGTGATCCTGTTTGAAAAACTGGGTCTGCCGGTTATCAAAAAAA
CGAAAACCGGTTATAGCACCGCAGCAGATGTTCTGGAAAAACTGAAATCAGAACATCA
GATTGTGCAGCTGATTCTGGAATATCGTACCCTGGCCAAACTGCAGAGCACCTATATTG
AAGGTCTGATCAAAGAAGTGCATCCGAAAGATAGCAAAGTGCATACCCGTTTTATGCAG
GCACTGACCAGCACCGGTCGTCTGAGCAGCACCGATCCGAATCTGCAGAATATTCCGA
TTCGTCTGGAAGAAGGTCGTAAAATTCGCAAAGCCTTTGTGCCGAGCCATGATGGTTG
GCTGCTGTTTAGCGCAGATTATAGCCAGATTGAACTGCGTGTTCTGGCACATATGAGC
AAAGATAAAAATCTGGTGGAAGCCTTTAACCAAGGCATGGATATTCATACCCGTACCGC
AATGGAAGTTTTTCATGTTAGCCAGGATGATGTGACCAGCAATATGCGTCGTGCAGCAA
AAGCAGTTAATTTCGGTATTATCTATGGCATTAGCGCATATGGTCTGAGCCAGAATCTG
GATATTTCACGTAAAGAAGCAGGCGAATTCATCGAGAAATACTTTGAAAGTTTTCCGGG
TGTGAAAGAATATATGGACAACATTGTTCAAGAGGCAAGCTGAAAGGTTATGTTACCA
CCATTCTGAATCGTCGTCGTTATCTGCCGGATATTACCAGCAAAAATTTCAATCTGCGT
AGCTTTGCAGAACGTACCGCCATGAATACCCCGATTCAGGGTAGCGCAGCCGATATCA
TCAAAAAAGCAATGCTGGATATTGATGCCCGTCTGAATAGCGAAGGTCTGCAGGCAAA
ACTGCTGCTGCAGGTTCACGATGAACTGATTTTTGAAGCACCGAAAGAAGAGATCGAG
AAGCTGGAAAAAATTGTTCCGGAAGTTATGGAAAGTGCCATTCTGCTGGATGTTCCGCT
GAAAGTTGATATTAGCTATGGTGAAACCTGGTACGATGCCAAATAA The invention will now be described by way of a non-limiting Example with reference to the following figures in which:

FIG. 1 gives the sequence of a region within the finger domain of DNA polymerase I from a number of species which may be modified in accordance with the present invention. The key aspartic acid residue is in bold type.

FIG. 2 shows an overview of the strand-displacement activity assay setup. F=fluorophore. Q=Quencher.

Figure 5:
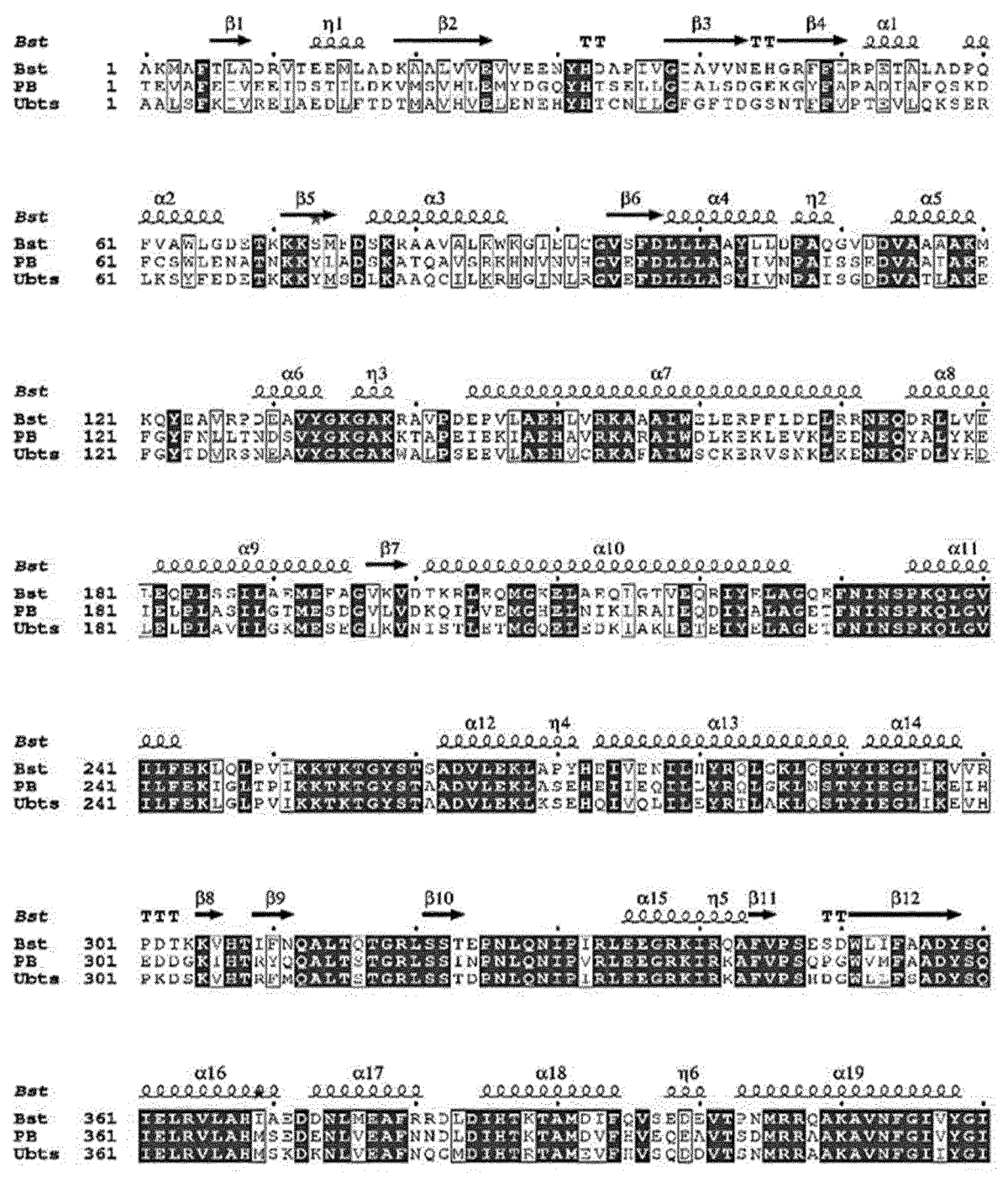
Figure 5:
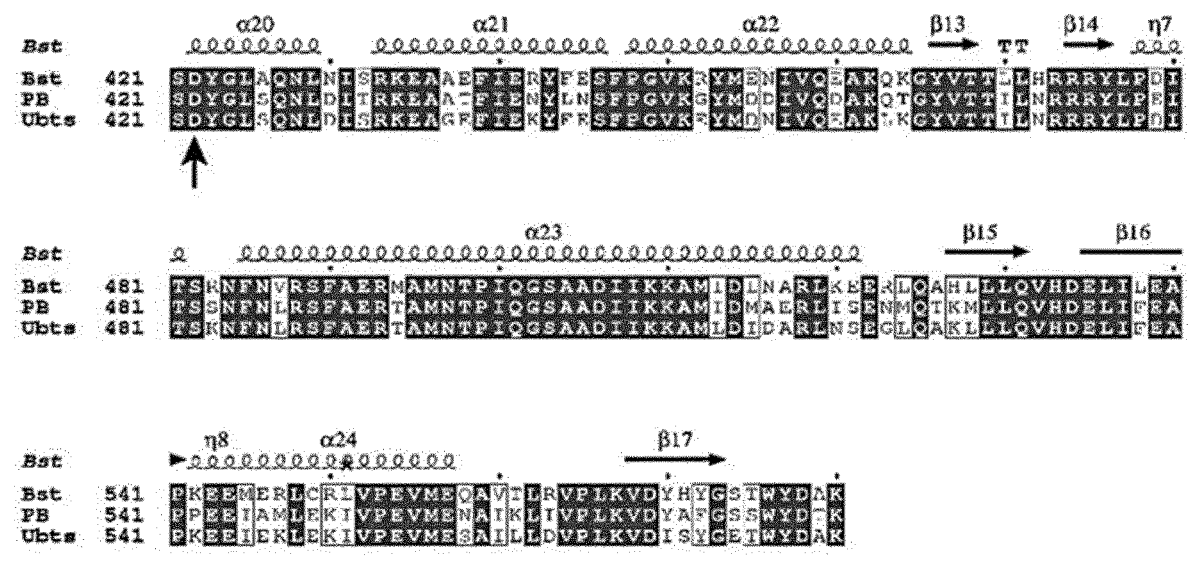

FIG. 5 is a sequence alignment of the wild type (truncated) amino acid sequences of the DNA polymerases from PB, Bst and Ubts. The large arrow indicates the 422 position where the Asp (D) is mutated to Ala (A). The alignment is produced using Clustal X2 and is visualised using ESPript 3.0 server.

Figure 6:
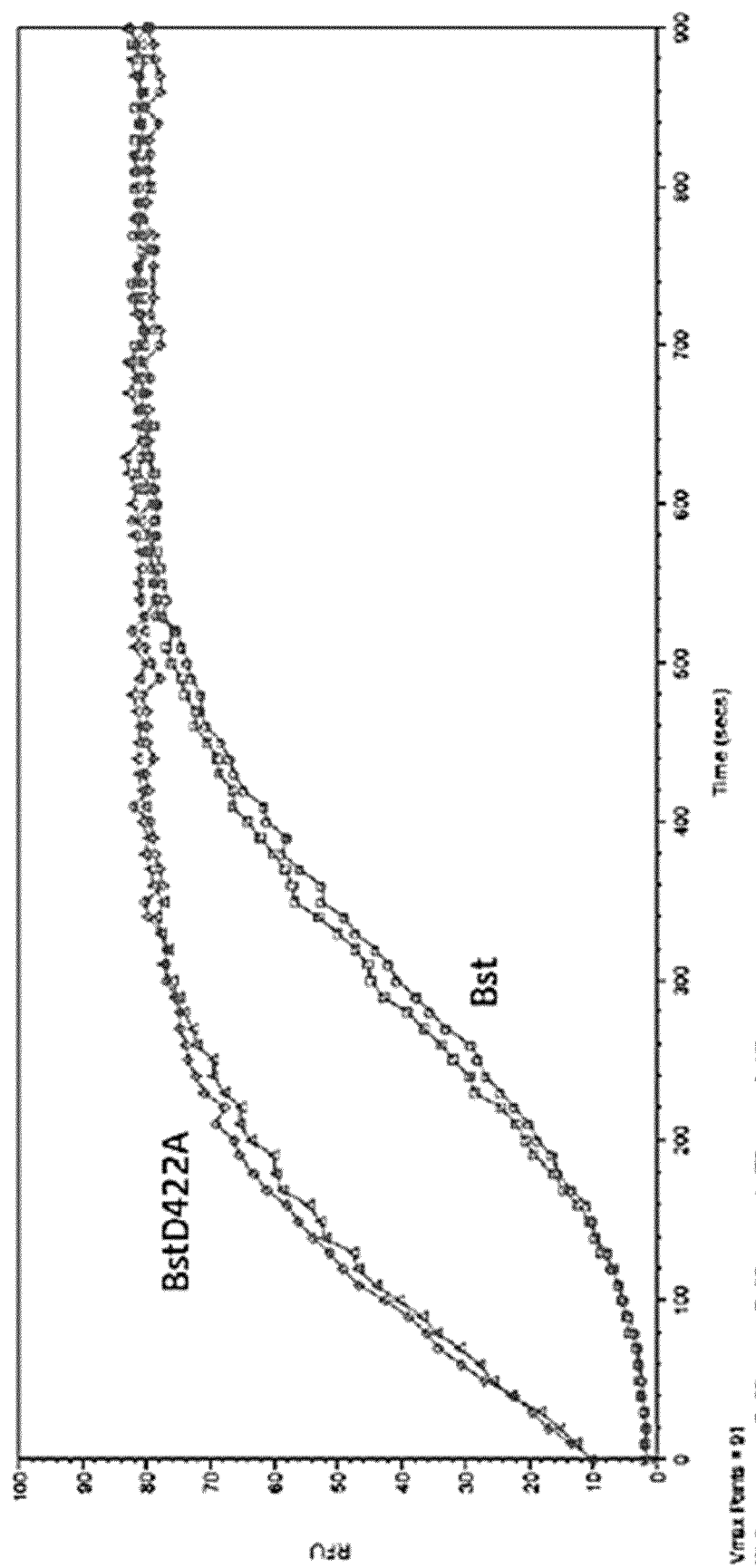

FIG. 6 shows the effect of the D422A mutation on strand-displacement activity of *Bacillus stearothermophilus* (large fragment) polymerase I (Bst) at 37° C. in presence of 10 mM KCl.

Figure 7:
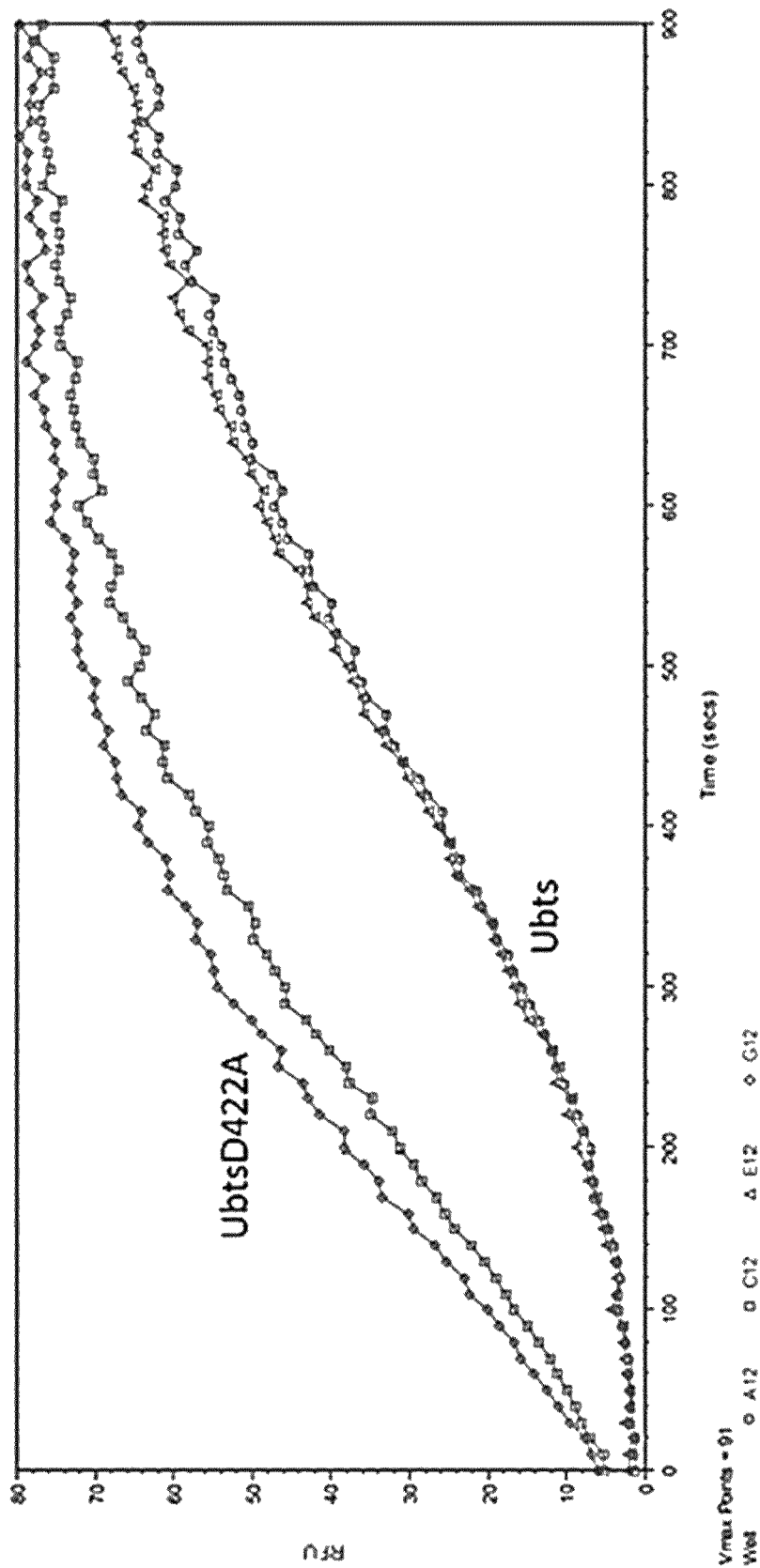

FIG. 7 shows the effect of the D422A mutation on strand-displacement activity of *Ureibacillus thermosphaericus* (large fragment) Polymerase I (Ubts) at 37° C. in presence of 10 mM KCl.

EXAMPLES

Example 1

Cloning of Sequences
PB Polymerase I Wild Type (Large Fragment) and D422A Mutant
The gene (SEQ ID NO: 3) encoding the DNA polymerase I large fragment (i.e. omitting the 5'-3' exonuclease domain of the protein) from the *Psychrobacillus* sp. was cloned into the vector pET151/D-TOPO®. The codon-optimised variant also containing the D422A mutation (SEQ ID NO: 13) was cloned into the vector pET-11a. In each case the construct encoded a His$_6$ tag at the N-terminus of the polymerase followed by the recognition sequence for the TEV protease, thus allowing cleavage of the tag.
Bst Polymerase I (Large Fragment) and Ubts Polymerase I (Large Fragment) and their D422A Mutant
The codon-optimized genes encoding the polymerase I large fragment from *Geobacillus stearothermophilus* (Bst) and *Ureibacillus thermosphaericus* (Ubts, Genbank accession nr. WP_016837139) were purchased from the Invitrogen GeneArt Gene Synthesis service from Thermo Fisher Scientific. The genes (SEQ ID NOS: 14 and 15) were cloned into the vector pTrc99A encoding an N-terminal His$_6$-tag by FastCloning (Li et al. (2011), BMC Biotechnology, 11:92). The corresponding mutation from Asp to Ala at position 422 (PB polymerase I large fragment) was introduced using the QuikChange II Site-Directed Mutagenesis Kit (Agilent Technologies) and confirmed by sequence analysis.
Protein Production and Purification
PB Polymerase I Wild Type (Large Fragment) and D422A Mutant
Recombinant protein production was performed in Rosetta 2 (DE3) cells (Novagen®). The cells grew in Terrific Broth media and gene expression was induced at $OD_{600\,nm}$ 1.0 by addition of 0.1 mM IPTG. Protein production was carried out at 15° C. for 6-8 h. For protein purification the pellet of a 1-I cultivation was resuspended in 50 mM HEPES, 500 mM NaCl, 10 mM imidazole, 5% glycerol, pH 7.5, 0.15 mg/ml lysozyme, 1 protease inhibitor tablet (cOmplete™, Mini, EDTA-free Protease Inhibitor Cocktail, Roche) and incubated on ice for 30 min. Cell disruption was performed by French press (1.37 kbar) and subsequently by sonication with the VCX 750 from Sonics® (pulse 1.0/1.0, 5 min, amplitude 25%). In the first step the soluble part of the $His_6$-tagged protein present after centrifugation (48384 g, 45 min, 4° C.) was purified by immobilized $Ni^{2+}$-affinity chromatography. After a wash step with 50 mM HEPES, 500 mM NaCl, 50 mM imidazole, 5% glycerol, pH 7.5 the protein was eluted at an imidazole concentration of 250 mM and further transferred into 50 mM HEPES, 500 mM NaCl, 10 mM $MgCl_2$, 5% glycerol, pH 7.5 by use of a desalting column.

The second step was cleavage of the tag by TEV protease performed over night at 4° C. in 50 mM Tris pH 8.0, 0.5 mM EDTA and 1 mM DTT. To separate the protein from the $His_6$-tag and the $His_6$-tagged TEV protease a second $Ni^{2+}$-affinity chromatography has been performed in the third step by applying 50 mM HEPES, 500 mM NaCl, 5% glycerol, pH 7.5. Fourth and final step of the protein purification was size-exclusion chromatography on a HiLoad 16/600 Superdex 200 pg (GE Healthcare) in 50 mM HEPES, 500 mM NaCl, 5% glycerol, pH 7.5. The final protein solution was concentrated and stored with 50% glycerol at −20° C.

Bst Polymerase I and Ubts Polymerase I (Large Fragment) and their D422A Mutants

Recombinant protein production for Bst and Ubts polymerase I (large fragment) and their D422A mutant was performed in Rosetta 2 (DE3) cells (Novagen®). Cells grew in Luria Bertani media at 37° C. and gene expression was induced at $OD_{600\,nm}$ 0.5 by addition of 0.5 mM IPTG. Protein production was carried out at 37° C. for 4 h. For protein purification the pellet of a 0.5-I cultivation was resuspended in 50 mM Tris pH 8.0, 300 mM NaCl, 1 mM EDTA, 1 mM DTT, 10 mM imidazole, 0.15 mg/ml lysozyme, 1 protease inhibitor tablet (cOmplete™, Mini, EDTA-free Protease Inhibitor Cocktail, Roche) and incubated on ice for 30 min. Cell disruption was performed by sonication with the VCX 750 from Sonics® (pulse 1.0/1.0, 15 min, amplitude 25%). The soluble part of the $His_6$-tagged protein present after centrifugation (48384 g, 45 min, 4° C.) was purified by immobilized $Ni^{2+}$-affinity chromatography. After a wash step with 50 mM Tris pH 8.0, 300 mM NaCl, 1 mM EDTA, 1 mM DTT, 10 mM imidazole the protein was elution with gradually increasing the imidazole to 500 mM. Fractions containing the protein were collected and buffer exchange was performed into 20 mM Tris pH 7.1, 100 mM KCl, 2 mM DTT, 0.2 mM EDTA and 0.2 Triton X-100 by desalting. The final protein solution was concentrated and stored with 50% glycerol at −20° C.

Activity Measurements
Polymerase Activity

The polymerase activity assay is based on a molecular beacon assay (modified from Summerer (2008), Methods Mol. Biol.; 429: 225-235). The molecular beacon template consists of a 23mer loop that is connected by a GC-rich 8mer stem region (sequence is indicated in italics) and a 43mer 3' extension. Due to the stem-loop structure the FAM (donor) and Dabcyl (acceptor, non-fluorescent quencher) molecules are in close proximity and thus the FAM fluorescence signal is quenched. Upon primer extension by the DNA polymerase the stem is opened and the increase in distance of the two dyes is measured by the restoration of FAM fluorescence as relative fluorescence units in appropriate time intervals by exciting at 485 nm and recording emission at 518 nm. The measurement was performed in a SpectraMax® $M2^e$ Microplate Reader (Molecular Devices).

```
molecular beacon template
                                              (SEQ ID NO: 16)
5'-
GGCCCGT^{Dabcyl}AGGAGGAAAGGACATCTTCTAGCAT^{FAM}ACGGGCCGT-
CAAG
TTCATG GCCAGTCAAGTCGTCAGAAATTTCGCACCAC-3' primer
                                              (SEQ ID NO: 17)
5'-GTGGTGCGAAATTTCTGAC-3'
```

The molecular beacon substrate was produced by incubating 20 µl of 10 µM molecular beacon template and 15 µM primer in 10 mM Tris-HCl pH 8.0, 100 mM NaCl for 5 min at 95° C. The reaction was then let to cool down at room temperature for 2 h. The substrate solution was stored at −20° C. with a final concentration of 10 µM.

Assay Set-Up for Analyzing Effect of Different [Salt] on Polymerase Activity of PB and Pb D422A Fifty microliter reactions consisted of 200 nM substrate and 200 µM dNTP (equimolar amounts of dATP, dGTP, dCTP and dTTP). The reaction further contained 5 mM $MgCl_2$ in 50 mM BIS-Tris propane at pH 8.5, 1 mM DTT, 0.2 mg/ml BSA and 2% glycerol. Final salt concentration in the reaction buffer has been adjusted to 25 mM, 40 mM, 60 mM, 80 mM, 110 mM, 160 mM and 210 mM NaCl or KCl for PB and 20 mM, 40 mM, 60 mM, 80 mM, 100 mM, 150 mM and 200 mM NaCl or KCl for PB D422A. The activity assay was carried out at 25° C. in black 96-well fluorescence assay plates (Corning®). The reaction was initiated by addition of protein solution, i.e. addition of polymerase.

Figure 4:
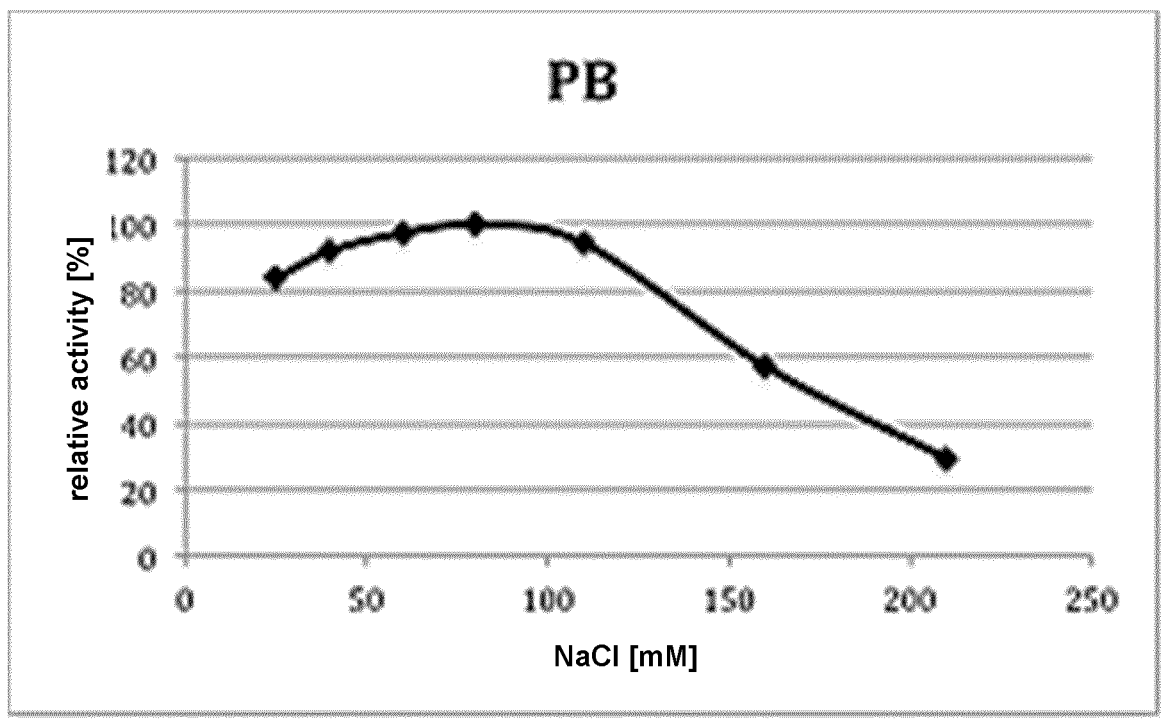
FIG. 4 shows the polymerase activity of wild type and mutant PB polymerase at various NaCl and KCl concentrations (25° C.).
Figure 4:
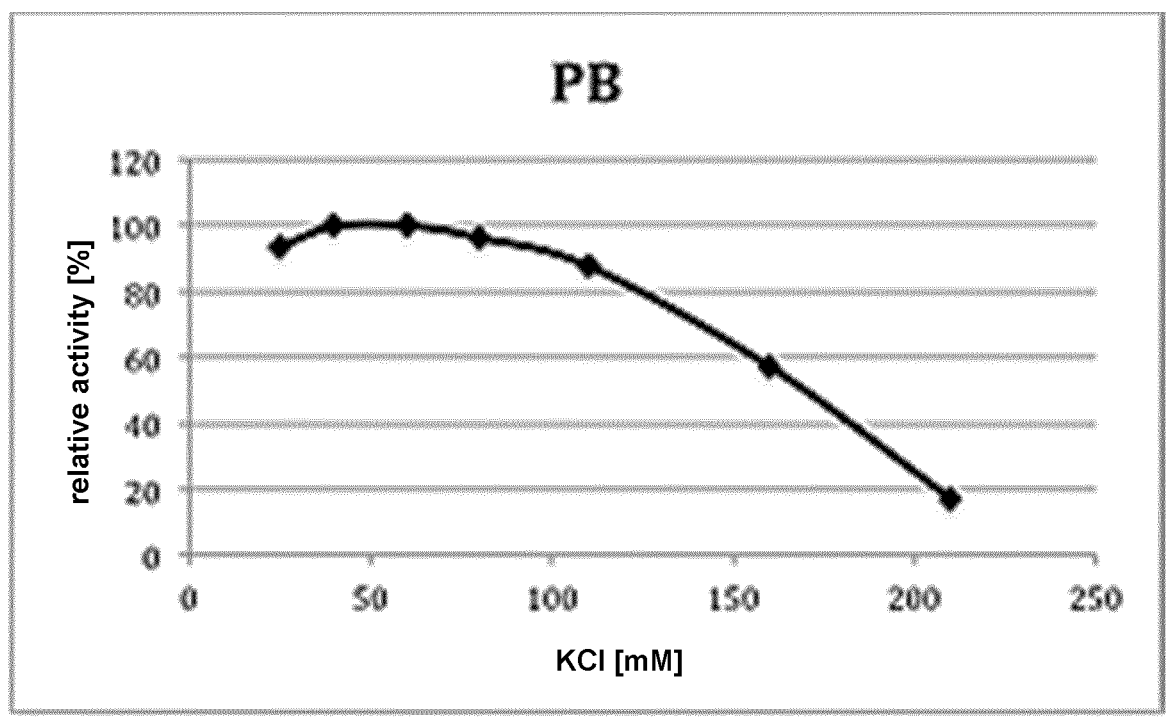
Figure 4:
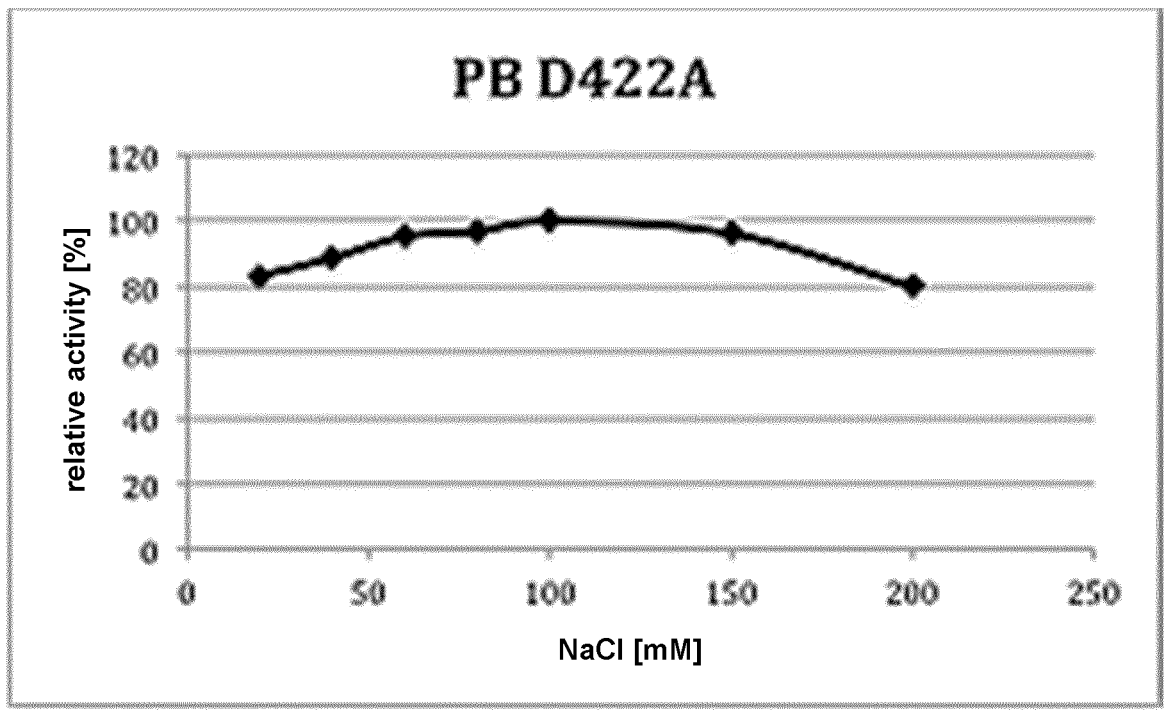
Figure 4:
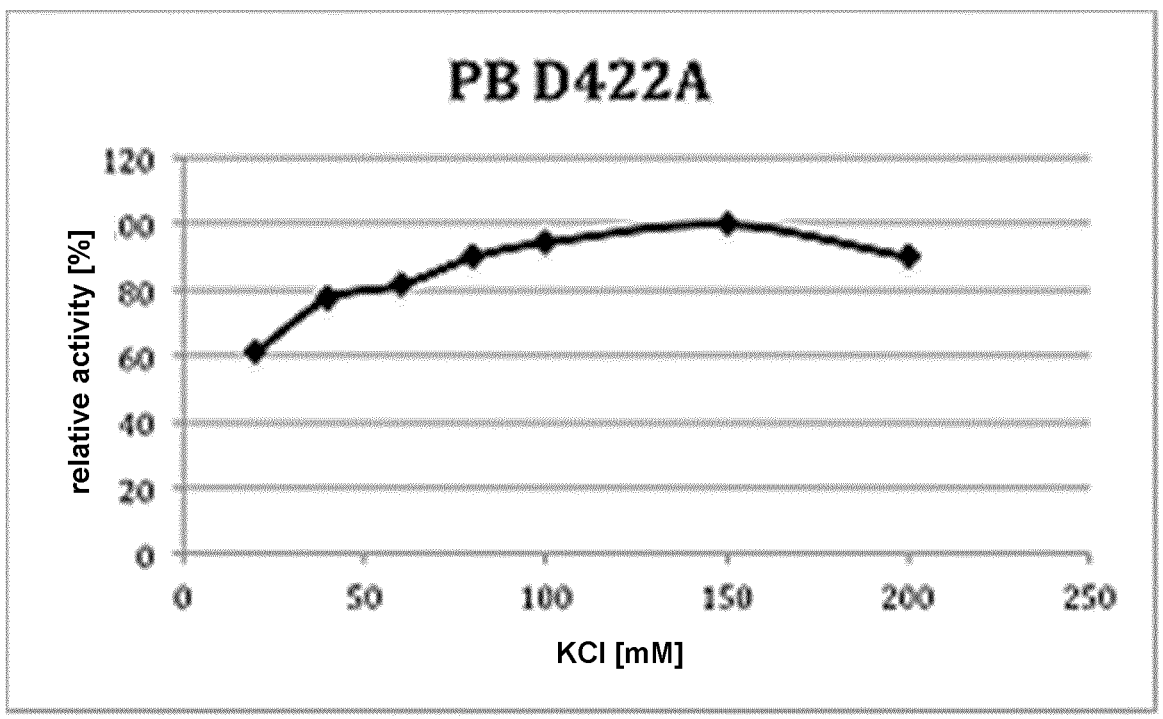

Results are shown in FIG. 4.

Assay Set-Up for Analyzing Specific Polymerase Activity of PB and PB D422A at 100 mM, 150 mM and 200 mM NaCl Fifty microliter reactions consisted of 200 nM substrate and 200 µM dNTP (equimolar amounts of dATP, dGTP, dCTP and dTTP). The reaction further contained 5 mM $MgCl_2$ in 50 mM BIS-Tris propane at pH 8.5, 1 mM DTT, 0.2 mg/ml BSA and 2% glycerol. Final salt concentration in the reaction buffer has been adjusted to 100 mM, 150 mM and 200 mM NaCl, respectively. The assay was carried out at 25° C. in black 96-well fluorescence assay plates (Corning®). The reaction was initiated by addition of protein solution, i.e. addition of polymerase.

Results are shown in Table 3 (at end of Example).

Strand-Displacement Activity Assay

Figure 2:
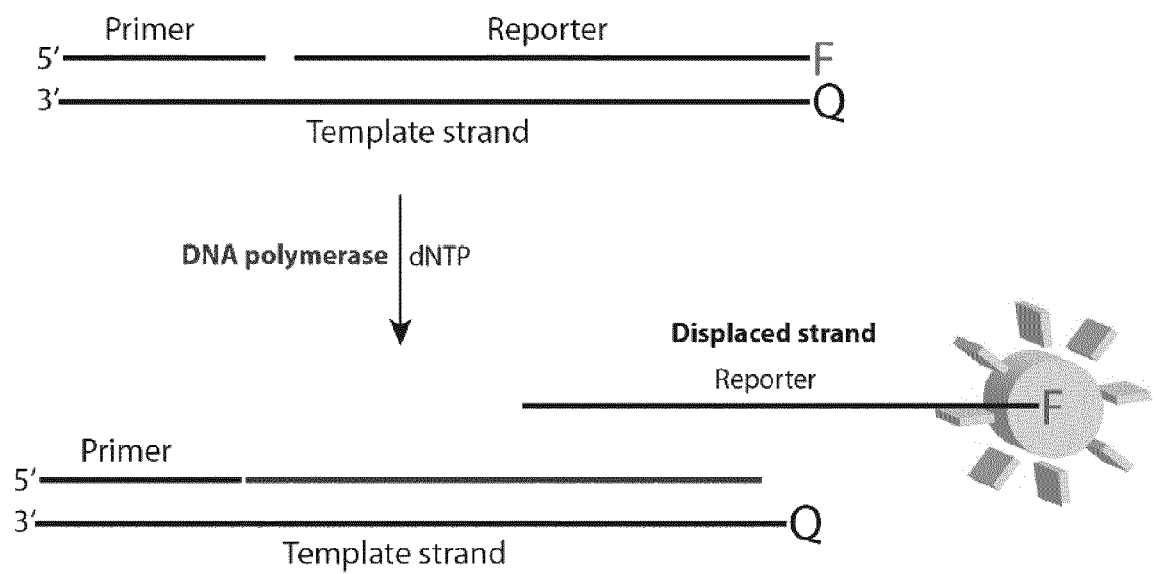

An overview of the assay setup is shown in FIG. 2. The assay is based on an increase in fluorescence signal that is measured upon displacement of the quenched reporter strand which is only achievable through strand-displacement activity of the DNA polymerase.

The substrate for the strand-displacement activity assay consists of a "cold" primer of 19 oligonucleotides (SEQ ID NO:18) and a reporter strand consisting of 20 oligonucleotides that is labeled with the TAMRA fluorophore (F) at its 3' end (SEQ ID NO:19). The template strand consists of 40 oligonucleotides and is labeled with the Black Hole Quencher 2 (BHQ2) at its 5' end (SEQ ID NO:20). The primers are annealed to the template strand leaving a one nucleotide gap at position 20 on the template strand. The labels are in close proximity and thus the fluorophore TAMRA is quenched by BHQ2. Upon strand-displacement activity of the DNA polymerase I the TAMRA labeled oligonucleotide is displaced from the template strand. As a consequence the fluorophore and the quencher are no longer in close proximity and an increase in TAMRA fluorescence can be measured as relative fluorescence units in appropriate time intervals (excitation 525 nm, emission 598 nm, SpectraMax® M2$^e$ Microplate Reader (Molecular Devices)).

```
5'-TATCCACCAATACTACCCT CGATACTTTGTCCACTCAAT
[TAMRA]-3'

3'-ATAGGTGGTTATGATGGGATGCTATGAAACAGGTGAGTTA
[BHQ2]-5'
```

The substrate for the strand-displacement activity assay was produced by incubating 20 µl of 10 µM "cold" primer, 10 µM reporter strand and 10 µM template strand in 10 mM Tris-HCl pH 8.0, 100 mM NaCl at 95° C. for 5 min. The reaction was then let to cool down at room temperature for 2 h. The substrate solution was stored at −20° C. with a final concentration of 10 µM.

Assay Set-Up for Comparison of the Specific Strand-Displacement Activity of PB, PB D422A and Commercially Known Polymerases Fifty microliter reactions consisted of 200 nM substrate and 200 µM dNTP (equimolar amounts of dATP, dGTP, dCTP and dTTP). For PB polymerase I the reaction further contained 5 mM MgCl$_2$ in 50 mM BIS-TRIS propane at pH 8.5, 100 mM NaCl, 1 mM DTT, 0.2 mg/ml BSA and 2% glycerol. For the commercially known polymerase Is the respective reaction buffer supplied by New England Biolabs have been used. Final salt concentration in the reaction buffer has been adjusted to 100 mM according to the optimal salt for the respective polymerases. The activity assay was carried out at 25° C. in black 96-well fluorescence assay plates (Corning®). The reaction was initiated by addition of protein solution (i.e. addition of polymerase).

Figure 3:
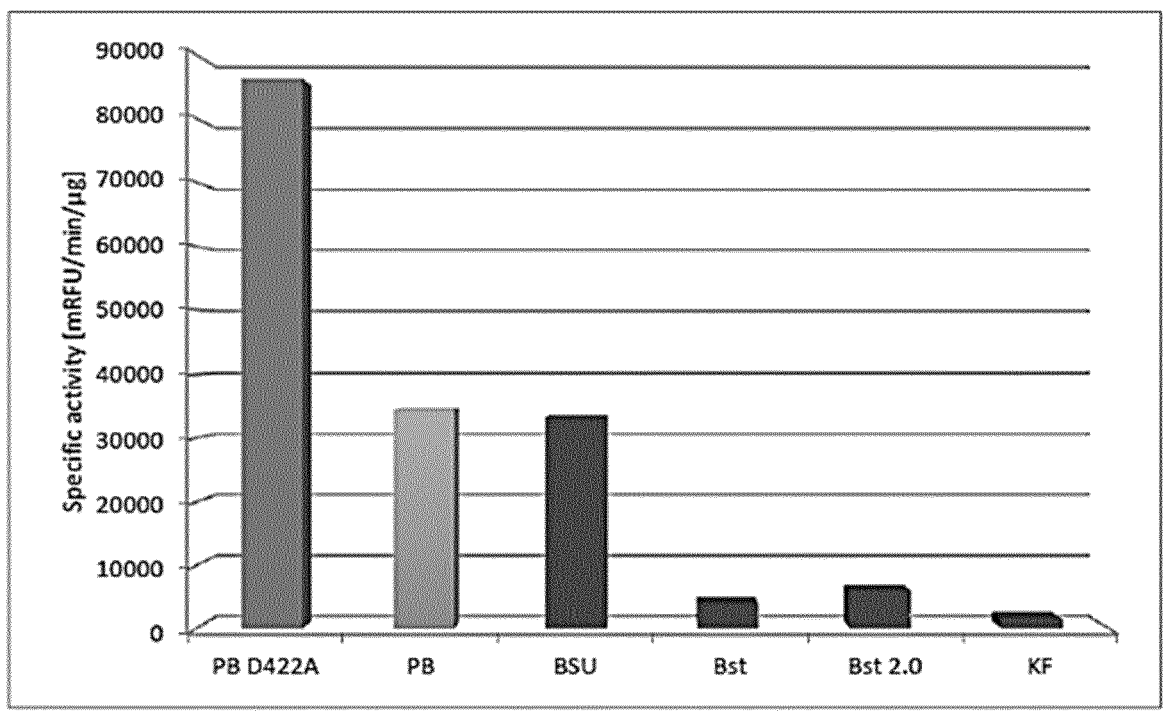
FIG. 3 shows a comparison of the strand-displacement activity at 25° C. of PB and the PB D422A mutant as well as for various commercial enzymes including the Klenow fragment (KF).

Results are shown in FIG. 3.

Assay Set-Up for Specific Strand-Displacement Activity of PB and PB D422A at 100 mM, 150 mM and 200 mM NaCl Fifty microliter reactions consisted of 200 nM substrate and 200 µM dNTP (equimolar amounts of dATP, dGTP, dCTP and dTTP). The reaction further contained 5 mM MgCl$_2$ in 50 mM BIS-Tris propane at pH 8.5, 1 mM DTT, 0.2 mg/ml BSA and 2% glycerol. Final salt concentration in the reaction buffer has been adjusted to 100 mM, 150 mM and 200 mM NaCl, respectively. The assay was carried out at 25° C. in black 96-well fluorescence assay plates (Corning®). The reaction was initiated by addition of protein solution, i.e. addition of polymerase.

Results are shown in Table 2 below.

Assay Set-Up for Analyzing Strand-Displacement Activity of Bst/BstD422A and Ubts/UbtsD422A Fifty microliter reactions consisted of 200 nM substrate and 200 µM dNTP (equimolar amounts of dATP, dGTP, dCTP and dTTP). The reaction further contained 20 mM Tris pH 7.9 (at 25°), 10 mM KCl, 10 mM (NH$_4$)$_2$SO$_4$, 2 mM MgSO$_4$, 0.1% Triton X-100.

The assay was carried out at 37° C. in black 96-well fluorescence assay plates (Corning®). The reaction was initiated by addition of protein solution (20 ng for Bst and BstD422A, 100 ng for Ubts and UbtsD422A), i.e. addition of polymerase. For determination of the specific strand-displacement activity (mRFU/min/µg) at a higher KCl the final concentration has been set to 150 mM KCl. The increase in TAMRA fluorescence was measured as relative fluorescence units in appropriate time intervals by exciting at 525 nm and recording emission at 598 nm. The measurement was performed in a SpectraMax® M2$^e$ Microplate Reader (Molecular Devices).

Results based on this strand-displacement activity assay are shown in FIGS. 6 and 7 and Table 4 below. The mutant enzymes all show enhanced activity.

Tables

TABLE 1

Summary of different enzymatic properties for wtPB and the D422A mutant (at 25° C.).

| Variant | Strand-displacement activity (100 mM NaCl) | Polymerase activity (100 mM NaCl) | T$_m$ | MgCl$_2$ | NaCl KCl (>80% activity) | pH |
|---|---|---|---|---|---|---|
| PB D422A | 310% | 120% | 44.8° C. | 4-6 mM | 25-200 mM<br>40-200 mM | 8.5 |
| PB pol I wild type | 100% | 100% | 44.8° C. | 3-8 mM | 25-125 mM<br>25-115 mM | 8.5 |

TABLE 2

Strand-displacement activity of PB D422A mutant
compared to wtPB in presence of 100-200 mM NaCl.
Strand-displacement activity

| | Activity [mRFU/min/µg] | | |
|---|---|---|---|
| NaCl | wtPB | PBD422A | Ratio (PB D422A/wtPB) |
| 100 | 9.35E+04 | 28.8E+04 | 3.1 |
| 150 | 7.54E+04 | 20.5E+04 | 2.7 |
| 200 | 4.65E+04 | 18.1E+04 | 3.9 |

TABLE 3

DNA polymerase activity of PB D422A mutant
compared to wt PB in presence of 100-200 mM NaCl.
Polymerase activity

| | Activity [mRFU/min/µg] | | |
|---|---|---|---|
| NaCl [mM] | wtPB | PBD422A | Ratio (PB D422A/wtPB) |
| 100 | 1.42E+06 | 1.66E+06 | 1.2 |
| 150 | 1.02E+06 | 1.50E+06 | 1.5 |
| 200 | 0.55E+06 | 1.37E+06 | 2.5 |

TABLE 4

Strand-displacement activity of the D422A mutants of Bst and Ubts
compared to wt enzymes in presence of 150 mM KCl.

| SDA(mRFU/min/µg) | | Ratio BstD422A/ Bst | SDA (mRFU/min/µg) | | Ratio UbtsD422A/ Ubts |
|---|---|---|---|---|---|
| Bst (wt) | BstD422A | | Ubts(wt) | UbtsD422A | |
| 3.52E+05 | 6.99E+05 | 2.0 | 0.59E+05 | 2.14E+05 | 3.6 |

Example 2

Further *Psychrobacillus* sp. (PB) DNA polymerase mutants were also made and tested:

Site-Directed Mutagenesis

The corresponding mutation from Asp to Ser, Lys, Val, Leu and Asn, respectively, at position 422 was introduced using the QuikChange II Site-Directed Mutagenesis Kit (Agilent Technologies).

D422V and D422L (hydrophobic residues of different lengths),

D422S (small hydrophilic),

D422N (larger hydrophilic) and

D422K (positively charged).

The starting point was the plasmid DNA of the D422A mutant. Mutations were confirmed by sequencing analysis.

Protein Production and Protein Purification

Recombinant protein production was performed in Rosetta 2 (DE3) cells (Novagen®). The cells grew in Terrific Broth media and gene expression was induced at $OD_{600\ nm}$ 1.0 by addition of 0.1 mM IPTG. Protein production was carried out at 15° C. for 6-8 h. For protein purification the pellet of a 50-ml cultivation was resuspended in 1 ml 50 mM HEPES, 500 mM NaCl, 10 mM imidazole, 5% glycerol, pH 7.5, 0.15 mg/ml lysozyme and incubated on ice for 20 min. Cell disruption was performed by sonication with the VCX 750 from Sonics® (pulse 1.0/1.0, 1 min, amplitude 20%).

The soluble part of the $His_6$-tagged protein present after centrifugation (16000 g, 30 min, 4° C.) was purified with PureProteome™ Magnetic Beads (Millipore) and eluted in 50 µl 50 mM HEPES, 500 mM NaCl, 500 mM imidazole, 5% glycerol, pH 7.5.

The strand-displacement assay was performed as described in Example 1.

All these other mutants performed better in assays of strand displacement activity (data not shown) as compared to the wt PB polymerase, but not as well as the PB D422A mutant.

The invention claimed is:

1. A DNA polymerase comprising the amino acid sequence of SEQ ID NO:2 or a variant sequence which is at least 70% identical to SEQ ID NO:2, wherein an aspartic acid residue at position 422 of SEQ ID NO:2, or an equivalent aspartic acid residue at an equivalent position in the variant sequence, is replaced by alanine.

2. The DNA polymerase according to claim 1, wherein said DNA polymerase comprises an amino acid sequence which is at least 80% identical to SEQ ID NO:2, wherein the aspartic acid residue at position 422 of SEQ ID NO:2, or the equivalent aspartic acid residue in the variant sequence, is replaced by alanine.

3. The DNA polymerase according to claim 1, wherein said DNA polymerase comprises the amino acid sequence of SEQ ID NO: 2, or an amino acid sequence which is at least 90% identical to SEQ ID NO: 2, wherein the aspartic acid residue at position 422 of SEQ ID NO: 2, or the equivalent aspartic acid residue at the equivalent position in the variant sequence, is replaced by alanine.

4. The DNA polymerase according to claim 1, wherein said DNA polymerase comprises an amino acid sequence which is at least 70% identical to SEQ ID NO: 4, wherein an aspartic acid residue at position 719 of SEQ ID NO. 4, or an equivalent aspartic acid residue at an equivalent position in the variant sequence, is replaced by alanine.

5. The DNA polymerase according to claim 1, wherein said DNA polymerase has at least 30% greater strand displacement activity as compared to a DNA polymerase with SEQ ID NO:2 but with aspartic acid at position 422, relative to SEQ ID NO:2, or at the equivalent position in the variant sequence.

6. The DNA polymerase according to claim 1, wherein across a concentration range from 20 mM to 200 mM of NaCl, KCl, or a mixture thereof, said DNA polymerase exhibits at least 40% of its maximum polymerase activity.

7. A composition, comprising:
the DNA polymerase according to claim 1, and
a buffer.

8. A nucleic acid molecule, comprising:
a nucleotide sequence encoding the DNA polymerase according to claim 1.

9. The nucleic acid molecule of claim 8, wherein the nucleotide sequence has at least 70% sequence identity to SEQ ID NO: 13.

10. An expression vector comprising the nucleic acid molecule of claim 8, and one or more regulatory sequences enabling transcription and translation of a protein encoded by said nucleic acid molecule.

11. A host cell or virus, comprising one or more expression vectors according to claim 10.

12. A host cell or virus, comprising one or more nucleic acid molecules according to claim 8.

13. A method of producing the DNA polymerase of claim 1, which comprises:
(i) culturing a host cell in a growth medium, wherein the host cell comprises one or more recombinant expression vectors or one or more nucleic acid molecules encoding the DNA polymerase according to claim 1, under conditions suitable for expression of the encoded DNA polymerase; and optionally
(ii) isolating the expressed DNA polymerase from the host cell or from the growth medium or supernatant of the growth medium.

14. A method of nucleotide polymerization, which comprises:
(i) providing a reaction mixture comprising:
the DNA polymerase according to claim 1,
a template nucleic acid molecule,
an oligonucleotide primer which is capable of annealing to a portion of the template nucleic acid molecule, and
one or more species of nucleotide; and
(ii) incubating said reaction mixture under conditions whereby the oligonucleotide primer anneals to the template nucleic acid molecule and said DNA polymerase extends said oligonucleotide primer by polymerizing one or more nucleotides.

15. The method of claim 14, wherein said method is performed at a constant temperature.

16. The method of claim 15, wherein said constant temperature is from 0° C. to 42° C.

17. The method of claim 15, wherein said constant temperature is from 10° C. to 25° C.

* * * * *